United States Patent
Reisch

(10) Patent No.: US 9,834,562 B2
(45) Date of Patent: Dec. 5, 2017

(54) 7 BETA-SUBSTITUTED 6A, 14A-ETHENOMORPHINANS AND 7BETA-SUBSTITUTED 6A, 14A-ETHANOMORPHINANS

(71) Applicant: RHODES TECHNOLOGIES, Coventry, RI (US)

(72) Inventor: Helge Alfred Reisch, Westerly, RI (US)

(73) Assignee: RHODES TECHNOLOGIES, Coventry, RI (US)

( * ) Notice: Subject to any disclaimer, the term of this patent is extended or adjusted under 35 U.S.C. 154(b) by 0 days.

(21) Appl. No.: 14/655,912

(22) PCT Filed: Dec. 23, 2013

(86) PCT No.: PCT/IB2013/002877
§ 371 (c)(1),
(2) Date: Jun. 26, 2015

(87) PCT Pub. No.: WO2014/102591
PCT Pub. Date: Jul. 3, 2014

(65) Prior Publication Data
US 2016/0068538 A1 Mar. 10, 2016

Related U.S. Application Data

(60) Provisional application No. 61/789,269, filed on Mar. 15, 2013, provisional application No. 61/747,741, filed on Dec. 31, 2012.

(51) Int. Cl.
*C07D 489/12* (2006.01)

(52) U.S. Cl.
CPC .................. *C07D 489/12* (2013.01)

(58) Field of Classification Search
None
See application file for complete search history.

(56) References Cited

U.S. PATENT DOCUMENTS

| 3,562,279 | A | * | 2/1971 | Brown | C07D 489/12 546/39 |
|---|---|---|---|---|---|
| 3,634,430 | A | | 1/1972 | Brown et al. | |
| 5,849,915 | A | | 12/1998 | Kim et al. | |
| 5,952,495 | A | | 9/1999 | Huang et al. | |
| 6,359,139 | B1 | | 3/2002 | Khetani et al. | |
| 6,723,894 | B2 | | 4/2004 | Fist et al. | |
| 8,357,802 | B2 | * | 1/2013 | Huang | C07D 489/08 546/44 |

(Continued)

FOREIGN PATENT DOCUMENTS

| CZ | 300 995 B6 | 10/2009 |
|---|---|---|
| EP | 0 915 094 B1 | 11/2007 |

(Continued)

OTHER PUBLICATIONS

Bentley, K.W. and Hardy, D.G., "Novel Analgesics and Molecular Rearrangements in the Morphine-Thebaine Group. I. Ketones Derived from 6,14-endo-Ethenotetrahydrothebaine," *Journal of the American Chemical Society* 89(13):3267-3273, American Chemical Society, United States (1967).

Bentley, K.W., et al., "Novel Analgesics and Molecular Rearrangements in the Morphine-Thebaine Group II. Alcohols Derived from 6,14-endo-Etheno- and 6,14-endo-Ethanotetrahydrothebaine," *Journal of the American Chemical Society* 89(13):3273-3280, American Chemical Society, United States (1967).

Bentley, K.W. and Hardy, D.G., "Novel Analgesics and Molecular Rearrangements in the Morphine-Thebaine Group. III. Alcohols of the 6,14-endo-Ethenotetrahydrooripavine Series and Derived Analogs of N-Allylnormorphine and -norcodeine," *Journal of the American Chemical Society* 89(13);3281-3292, American Chemical Society, United States (1967).

Biyashev, D., et al., "Biochemical characterisation of newly developed β-etorphine and β-dihydroetorphine derivatives," *European Journal of Pharmacology* 442(1-2):23-27, Elsevier Science B.V., Netherlands (2002).

Coop, A., et al., "Structural Determinants of Opioid Activity in the Orvinols and Related Structures: Ethers of Orvinol and Isoorvinol," *J. Med. Chem.* 43(9):1852-1857, American Chemical Society, United States (2000).

Derrick, I., et al., "Perchloric acid induced epimerisation of the thevinones: an improved synthesis of 7βdihydrothevinones," *Tetrahedron Letters* 41(39):7571-7576., Elsevier Science Ltd., England (2000).

(Continued)

*Primary Examiner* — Heidi Reese
(74) *Attorney, Agent, or Firm* — Sterne, Kessler, Goldstein & Fox P.L.L.C.

(57) ABSTRACT

The application is directed to a process for increasing the proportion of 7β-epimer in an 7α/7β-epimer mixture of a 7-substituted 6α,14α-ethenomorphinan or a 7-substituted 6α,14α-ethanomorphinan, and specifically of compounds of Formula (I), wherein G, $R^2$-$R^4$, and are defined as set forth in the specification. The application is also directed to a process for purifying the 7β-epimer from an 7α/7β-epimer mixture of a 7-substituted 6α,14α-ethenomorphinan or a 7-substituted 6α,14α-ethanomorphinan. The application is also directed to a process for preparing 7β-substituted compounds of Formula $V^b$ wherein G and $R^2$-$R^5$ are defined as set forth in the specification.

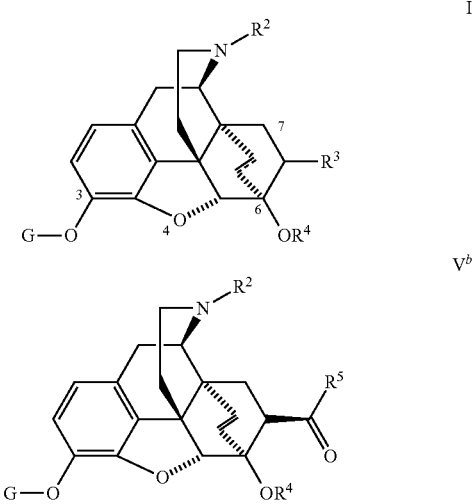

3 Claims, No Drawings

(56) References Cited

U.S. PATENT DOCUMENTS

| | | |
|---|---|---|
| 2008/0125592 A1 | 5/2008 | Huang |
| 2008/0312411 A1 | 12/2008 | Wolf et al. |
| 2009/0156817 A1 | 6/2009 | Wang et al. |
| 2010/0081813 A1 | 4/2010 | Orr et al. |
| 2010/0081816 A1 | 4/2010 | Mannino et al. |
| 2010/0087647 A1 | 4/2010 | Allen et al. |
| 2012/0010231 A1 | 1/2012 | Whitelock et al. |

FOREIGN PATENT DOCUMENTS

| | | |
|---|---|---|
| GB | 902659 | 8/1962 |
| GB | 937214 | 9/1963 |
| WO | WO 94/06426 A1 | 3/1994 |
| WO | WO 98/02033 A1 | 1/1998 |
| WO | WO 2006/035195 A1 | 4/2006 |
| WO | WO 2008/048957 A1 | 4/2008 |
| WO | WO 2010/039220 A1 | 4/2010 |
| WO | WO 2011/154826 A1 | 12/2011 |

OTHER PUBLICATIONS

Ghosh, A.C., et al., "Diels-Alder Reaction of βdihydrothebaine and Its 4-phenyl Ether With Methyl Vinyl Ketone: Synthesis of 6,14-exo-Ethenomorphinans," Part 7 in the series Novel Opiates and Antagonists, *The Journal of Organic Chemistry* 48(22):4137-4139, American Chemical Society, United States (1983).

Hutchins, C.W. and Rapoport, H., "Analgesics of the Orvinol Type. 19-Deoxy and 6,20-Epoxy Derivatives," *J. Med. Chem.* 27(4):521-527, American Chemical Society, United States (1984).

International Preliminary Report on Patentability for Application No. PCT/IB2013/002877, The International Bureau of WIPO, Geneva, Switzerland, dated Jun. 30, 2015, 6 pages.

International Search Report for Application No. PCT/IB2013/002877, European Patent Office, Rijswijk, Netherlands, dated Mar. 25, 2014, 4 pages.

Maat, L., et al., "Chemistry of Opium Alkaloids. Part 44: Synthesis and Opioid Receptor Binding Profile-of Substituted Ethenoisomorphinans and Ethenomorphinans," *Bioorganic & Medicinal Chemistry* 7(3);529-541, Elsevier Science Ltd., England (1999).

Marton, J., et al., "Herstellung von 6,14-Ethenomorphinan-Derivaten," *Monatshefte für Chemie* 125:1229-1239, Springer-Verlag, Austria (1994).

Marton, J., et al., "Isomerization Reactions of 7-substituted 6,14-Bridged Thebaine Derivatives (Bentley Compounds)," *Acta. Chemica Scandinavica* 52:1234-1238, Acta Chemica Scandinavica, United Kingdom (1998).

Marton, J., et al., "Synthesis of N-Substituted 7β-diprenorphine Derivatives," *Synthetic Communications* 25(6):829-848, Marcel Dekker, Inc., United States (1995).

Marton, J., et al., "Studies on the Synthesis of β-Thevinone Derivatives," *Tetrahedron* 54(31): 9143-9152, Elsevier Science Ltd., England (1998).

Uff, B.C., et al., "NMR Spectra and Stereochemistry of some 7-Substituted 6,14-Bridged Thebaine Derivatives,"*Magnetic Resonance in Chemistry* 23(6):454-459, Wiley Heyden Ltd., England (1985).

Written Opinion for Application No. PCT/IB2013/002877, European Patent Office, Munich, Germany, dated Mar. 25, 2014, 5 pages.

Wuts, P.G.M. and Greene, T.W., "Protection for the Hydroxyl Group, Including 1,2- and 1,3-Diols," in *Greene's Protective Groups in Organic Synthesis*, 4th Ed., Wuts, P.G.M. and Greene, T.W., eds., pp. 16-366, John Wiley & Sons, Inc., United States (2007).

Wuts, P.G.M. and Greene, T.W., "Protection for Phenols and Catechols," in *Greene's Protective Groups in Organic Synthesis*, 4th Ed., Wuts, P.G.M. and Greene, T.W., eds., pp. 367-430, John Wiley & Sons, Inc., United States (2007).

Bentley, K.W., "The Morphine Alkaloids, Diels-Alder Adducts of Thebaine and Related Compounds" *The Alkaloids: Chemistry and Physiology* 13:75-163, Academic Press, Inc., United States (1971).

Bentley, K.W., et al., "Novel Analgesics and Molecular Rearrangements in the Morphine-Thebaine Group. VI. Base-Catalyzed Rearrangements in the 6,14-endo-Ethenotetrahydrothebaine Series," *Journal of the American Chemical Society* 89(13):3312-3321, American Chemical Society, United States (1967).

Bentley, K.W. and Thomas, A.F., "The Morphine-Thebaine Group of Alkaloids. Part VI. The Condensation of Thebaine with Dienophils," *Journal of the Chemical Society Part 2*:1863-1867, The Chemical Society, England (1956).

Bentley, K.W., et al., "Novel Analgesics and Molecular Rearrangements in the Morphine-Thebaine Group. Part VIII. 7-Alkyl-6,14-endo-ethenotetrahydrothebaine and Related Compounds," *Journal of the Chemical Society* (C) Part 1:826-830, The Chemical Society, England (1969).

Bentley, K.W., et al., "Preparation of 7-(1,3,4-Oxadiazolyl)-6,14-endo-etheno-6,7,8,14-tetrahydrothebaines and Related Compounds as Potential Analgesics," *Journal of Medicinal Chemistry* 27;1276-1280, American Chemical Society, United States (1984).

Beyerman, H.C., et al., "Synthesis of peptide-morphinans based on Diels-Alder adducts of thebaine with enkephalin moieties (Chemistry of opium alkaloids, Part XVI)," *Recueil, Journal of the Royal Netherlands Chemical Society* 101(12):455-460, Royal Netherlands Chemical Society, Netherlands (1982).

Fulmor, W., et al., "Nuclear Magnetic Resonance Studies in the 6-14-endo-Ethenotetrahydrothebaine Series," *Journal of the American Chemical Society* 89(13):3322-3330, American Chemical Society, United States (1967).

Grivas, K., et al., "Acid Catalysed Rearrangements of the Thevinols: The Mechanism of Furanocodide Formation," *Tetrahedron Letters* 40:1795-1798, Elsevier Science Ltd., England (1999).

Husbands, S.M., et al., "Ring Constrained Analogues of the Orvinols: The Furanomorphides," *Bioorganic & Medicinal Chemistry Letters* 9(6):831-834, Elsevier Science Ltd., England (1999).

Johnson, R.E., et al., "Buprenorphine: Considerations for Pain Management," *Journal of Pain and Symptom Management* 29(3):297-326, Elsevier Inc., United States (2005).

Kim, K.J., et al., "Synthesis of a Conformationally-rigid Etorphine Analogous," *Bulletin of the Korean Chemical Society* 7(3):166-169, Korean Chemical Society, Korea (1986).

Lewis, J.W., et al., "Novel Analgesics and Molecular Rearrangements in the Morphine-Thebaine Group. Part XXVI. Some Reactions of the Thebaine-2-Chloro-acrylonitrile Adduct," Journal of the Chemical Society 6:878-881, The Chemical Society, England (1972).

Loew, G.H. and Berkowitz, D.S., "Effect of $C_7$ Substitution on Agonist/Antagonist Activity in Oripavines," *Characteristics and Functian of Opioids*, Van Ree, J.M. and Terenius, L., eds., pp. 223-224, Elsevier/North-Holland Biomedical Press, Netherlands (1978).

Mazza, S.M., "Determining C-7 Stereochemistry in C-7-Substituted 6α,14α-endo-Ethano- and 6α,14α-endo-Ethenotetrahydrothebaines by $^{13}C$ NWR; a Re-analysis," *Magnetic Resonance in Chemistry* 31:444-446, John Wiley & Sons, Ltd., England (1993).

Pindur, U., et al., "New Diels-Alder Reactions of (-)-Thebaine and First X-Ray Crystallographic Structure Analyses of the Cycloadducts," *Zeitschrift für Naturforschung B* 49b:272-279, Verlag der Zeitschrift für Naturforschung, Germany (1994).

Rosenbaum, J.S., et al., "Opiate Receptor Binding-Effect Relationship: Sufentanil and Etorphine Produce Analgesia at the μ-Site with Low Fractional Receptor Occupancy," *Brain Research* 291:317-324, Elsevier Science Publishers B.V., Netherlands (1984).

Rubinstein, R., et al., "Reactions of the Thebaine with Cis- and Trans- Disubstituted Dienophiles," *Tetrahedron* 30:1201-1210, Pergamon Press, Great Britain (1974).

English language Abstract of Czech Republic Patent Publication No. CZ 300 995 B6, Database of patents and utility models, Czech Republic Industrial Property Office (listed as document FP10 on the accompanying form PTO/SB/08A) (2009).

* cited by examiner

7 BETA-SUBSTITUTED 6A, 14A-ETHENOMORPHINANS AND 7BETA-SUBSTITUTED 6A, 14A-ETHANOMORPHINANS

BACKGROUND OF THE INVENTION

Field of the Invention

This application is in the field of medicinal chemistry. The application relates to a novel process for preparing 7β-substituted 6α,14α-ethenomorphinans and 7β-substituted 6α,14α-ethanomorphinans, and the pharmaceutically acceptable salts thereof. Particularly, the application relates to the selective precipitation of 7β-substituted 6α,14α-ethenomorphinans or 7β-substituted 6α,14α-ethanomorphinans from a mixture containing corresponding 7α-epimers by treating with an acid. Contrary to optical diastereomeric resolution of enantiomers (e.g., chiral bases) which requires chiral acids to resolve single enantiomers, the separation of the above-mentioned 7α/7β-epimers can be achieved even with achiral acids. The application also relates to the novel, isolated compounds and salts thereof.

Description of the Related Art

6α,14α-Ethenomorphinans and 6α,14α-ethanomorphinans are semi-synthetic oripavine or thebaine derivatives. The central structural element of this class of molecules is a morphinan ring system with an etheno or ethano bridge between the C-6 and C-14 carbons of the morphinan scaffold. Based on the nature of the carbon-carbon-bond between C-18 and C-19, these compounds are classified as 6α,14α-ethenomorphinans (carbon-carbon-double bond) or 6β,14α-ethanomorphinans (saturated carbon-carbon bond). The morphinan scaffold has the following structure:

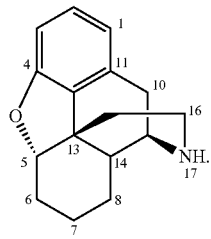

6α,14α-Ethenomorphinan derivatives with a substituent in the 7-position have been extensively studied over the last 60 years. During this time, drugs like Buprenorphine (Temgesic®, Subutex®, Suboxone®), Diprenorphine (Revivon®) and Etorphine (Immobilon®) were discovered. Buprenorphine is commercially the most important representative of this class of compounds and has been on the market since 1978 as a powerful analgesic and for the management of opioid dependence.

Buprenorphine, (2S)-2-[17-cyclopropylmethyl-4,5α-epoxy-3-hydroxy-6-methoxy-6α,14α-ethanomorphinan-7α-yl]-3,3-dimethylbutan-2-ol, a semi-synthetic opioid having the structure:

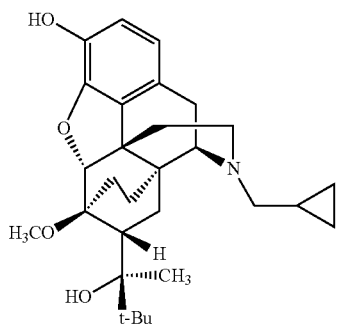 [SMILES: CO[C@]12CC[C@@]3(C[C@@H]1[C@](C)(O)C(C)(C)C)[C@H]1Cc4ccc(O)c5c4[C@@]3(CCN1CC1CC1)[C@H]2O5]

is used to treat opioid addiction, to control moderate acute pain in non-opioid tolerant individuals, and to control moderate chronic pain. Buprenorphine can be derived from either oripavine or thebaine: K. W. Bentley discovered buprenorphine using thebaine as the initial backbone structure. Thebaine is one of the main alkaloids in the Iranian poppy (*Papaver bracteatum*). Thebaine can also be isolated from *Papaver somniferum* which is also a source for oripavine (U.S. Pat. No. 6,723,894).

Buprenorphine has an extremely high binding affinity at the μ- and κ-opioid receptors. It has partial agonist activity at the μ-opioid receptor, partial or full agonist activity at the ORL-1/nociception and δ-opioid receptors, and competitive antagonist activity at the κ-opioid receptor. Buprenorphine exhibits an analgesic effect approximately 25 to 40 times more potent than morphine (by weight of equivalent low doses). Buprenorphine is marketed as oral formulations (tablets, sublingual tablets, and sublingual films), parenteral preparations, and transdermal patches.

All the above-mentioned drugs within this class of compounds contain an alkyl substituent attached to the nitrogen and a hydroxyl group attached to a lipophilic substituent in 7α-position of the C-ring. Through comparison of a large number of derivatives, it has become clear that the region above and away from C-7 has a significant impact on the μ-opioid receptor profile of these orvinols and related compounds (Hutchins et al., *J. Med. Chem.* 27:521-527 (1984); Coop et al., *J. Med. Chem.* 43:1852-1857 (2000).

This 7α-configuration (e.g. 7α-substituted 6α,14α-ethenomorphinan), found in all commercial drugs of this class of compounds, is however not a structural requirement for opioid receptor affinity, but rather a result of limited accessibility of the 7β-substituted derivatives (e.g. 7β-substituted 6α,14α-ethenomorphinan). The structures of 7α-6α,14α-ethenomorphinans/ethanomorphinans and 7β-6α,14α-ethenomorphinans/ethanomorphinans are shown in Figure 1 below:

FIGURE 1

Structure of 7α-substituted 6α,14α-ethenomorphinan/ethanomorphinan and 7β-substituted 6α,14α-ethenomorphinan/ethanomorphinan

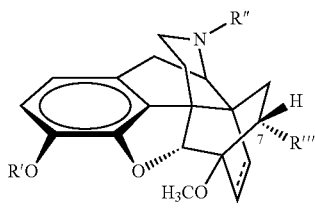

7α-substituted
6α, 14α-ethenomorphinan/
ethanomorphinan

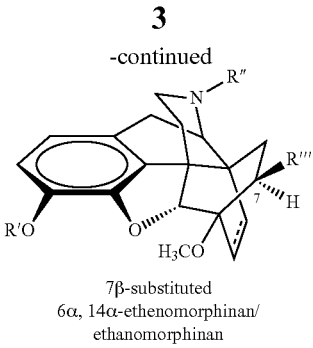

7β-substituted
6α,14α-ethenomorphinan/
ethanomorphinan

In Figure 1, ⫽ can be single bond or a double bond. Biochemical characterization of β-etorphine and β-dihydroetorphine derivatives indicate that the 7β-substituted derivatives have a comparable high affinity for opioid binding sites as their corresponding 7α-substituted analogs (Biyashev et al., *European Journal of Pharmacology* 442:23-27 (2002)). Although extensive SAR studies have not been reported for 7β-substituted 6α,14α-ethenomorphinans, the limited data available the for the β-substituted derivative of etorphine indicates that moving the substituent from position 7α to 7β decreased the affinity for the κ and δ receptor while the affinity for the μ receptor remained constant (Maat et al., *Bioorganic & Medicinal Chemistry* 7:529-541 (1999)).

Although the 7β-substituted derivatives of buprenorphine (Uff et al., *Magnetic Resonance in Chemistry* 23:6 (1985)) as well as the corresponding 7β-substituted derivatives of etorphine (Marton et al., *Tetrahedron* 54:9143-9152 (1998)), dihydroetorphine (Marton et al., supra) and diprenorphine (Marton et al., *Synth. Commun.* 25:829-848 (1995)), alongside the corresponding 7β-substituted process intermediates, were synthesized and characterized, little is generally known about the chemical or biological properties of 7β-substituted 6α,14α-ethenomorphinans or 7β-substituted 6α,14α-ethanomorphinans. In contrast, the 7α-substituted 6α,14α-ethenomorphinans and 7α-substituted 6α,14α-ethenomorphinans have been extensively studied and characterized.

7β-Substituted 6α,14α-ethenomorphinans and 7β-substituted 6α,14α-ethanomorphinans may be attractive chemotypes with potentially new pharmacological properties. However, the isolation processes of 7β-6α,14α-ethenomorphinans and 7β-6α,14α-ethanomorphinans described in the art require multiple process steps and afford the product only in a very low yield.

Accordingly, there is a need for an improved process for isolating 7β-substituted 6α,14α-ethenomorphinans and 7β-substituted 6α,14α-ethanomorphinans.

BRIEF SUMMARY OF THE INVENTION

The present disclosure provides a process for increasing the proportion of the 7β-epimer in an 7α/7β-epimer mixture of a 7-substituted 6α,14α-ethenomorphinan or a 7-substituted 6α,14α-ethanomorphinan. Said process comprises contacting a solution of the 7α/7β-epimer mixture with an acid to provide a precipitate, and isolating the precipitate to provide an isolated precipitate and a mother liquor. In one embodiment, the acid is an achiral acid. In another embodiment, the acid is a chiral acid.

In one embodiment, the present disclosure provides a process for increasing the proportion of the 7β-epimer in an 7α/7β-epimer mixture of compounds represented by Formula I, below. In one embodiment, the 7β-epimer is of Formula $V^b$, below.

In another embodiment, the present disclosure provides a process for purifying the 7β-epimer from a 7α/7β-epimer mixture of a 7-substituted 6α,14α-ethenomorphinan or a 7-substituted 6α,14α-ethanomorphinan. The process comprises contacting a solution of the 7α/7β-epimer mixture with an acid under conditions conducive to precipitation of the 7β-epimer, and then isolating the precipitate. The isolation of the precipitate leaves behind a residual mother liquor. In one embodiment, the acid is an achiral acid. In another embodiment, the acid is a chiral acid.

In another embodiment, the present disclosure provides a process for purifying the 7β-epimer from a 7α/7β-epimer mixture of compounds represented by Formula I, below. In one embodiment, the 7β-epimer is of Formula $V^b$, below.

The present disclosure also provides a process for preparing 7β-substituted compounds of Formula I, and the pharmaceutically acceptable salts thereof. The process comprises, conducting a Diels-Alder reaction to form a 7α/7β-epimer mixture; forming a first precipitate of the 7α/7β-epimer mixture; isolating the first precipitate from the reaction mixture to obtain a first mother liquor; optionally reducing the volume of the first mother liquor, and contacting the first mother liquor with an acid to provide a second precipitate; isolating the second precipitate to obtain the 7β-substituted compound as a salt and a second mother liquor; and optionally converting the salt into its free base. The second mother liquor is optionally epimerized and contacted with the acid to obtain the the 7β-substituted compound as a salt.

The present disclosure also provides novel isolated compounds of Formula I and salts thereof, and specifically compounds of Formula $V^b$ and salts thereof.

The present disclosure also provides Compounds

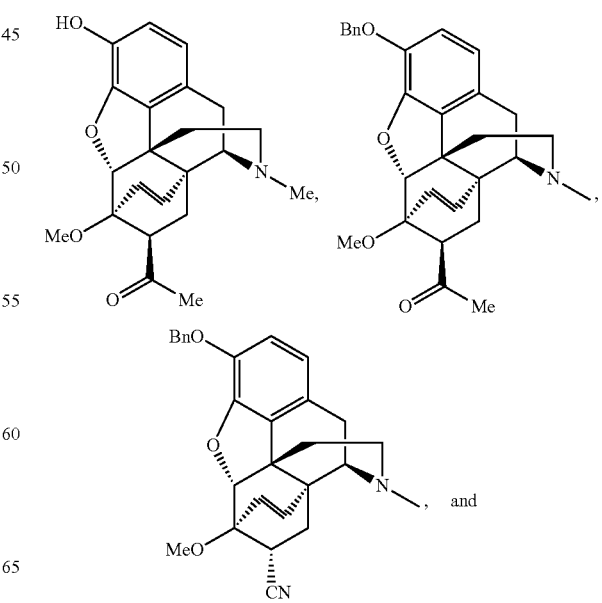

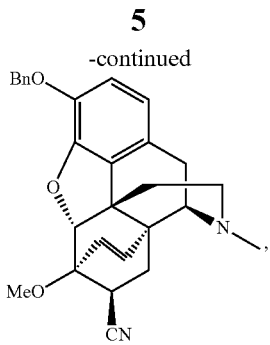

or a salt thereof. In another aspect of the present disclosure the use of these compounds or a salt thereof as a medicament is provided. In yet another aspect, the compounds or a salt thereof are used in treatment or prevention of pain, such as acute pain, chronic pain, or surgical pain. In yet another aspect, the present disclosure provides use of these Compounds of the Invention or a salt thereof in the manufacture of a medicament for treating or preventing pain, such as acute pain, chronic pain, or surgical pain. The present disclosure further provides methods of treating or preventing pain, comprising administering to a patient in need thereof a therapeutically effective amount of a Compound of the Invention. In certain embodiments, the pain includes acute pain, chronic pain, and surgical pain. In another aspect, the disclosure provides a pharmaceutical composition, comprising a therapeutically effective amount of any one of the above compounds or a pharmaceutically acceptable salt thereof, and one or more pharmaceutically acceptable carriers.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

6α,14α-Ethenomorphinans are synthesized in the literature using a synthetic pathway comprising of a Diels-Alder reaction between a morphinan-6,8-diene and a dienophile as shown below in Scheme 1. When thebaine (B) or oripavine (A) is the diene, the 6-methoxy group determines the stereo- and regioselectivity of the Diels-Alder reaction by polarizing the diene system, and the major product of the cycloaddition reaction is the 7α-substituted 6α,14α-ethenomorphinan along with a minor amount (~1-5%) of the 7β-substituted isomer (except for compounds where CN is in the position for R³, wherein the product of the cycloaddition reaction forms an about 1:1 mixture of 7α- and 7β-epimers). Due to a high regio-selectivity of the reaction, 8-substituted isomers are usually not observed at all (Bentley et al., *J. Am. Chem. Soc.* 89:3267-3273 (1967); Ghosh et al., *J. Org. Chem.* 48:4137-4139 (1983)).

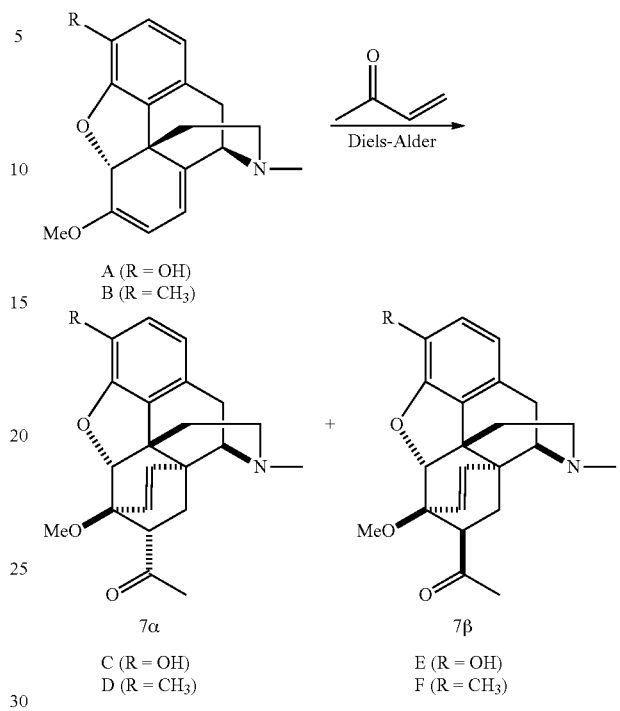

Scheme 1
Diels-Alder Reaction of Morphinan-6,8-dienes with methyl vinyl ketone

A (R = OH)
B (R = CH₃)

C (R = OH)
D (R = CH₃)

E (R = OH)
F (R = CH₃)

The 7α-substituted 6α,14α-ethenomorphinan is a precipitate that is isolated by a simple filtration and usually obtained in high purity without the need for an additional purification process. Since the 7α-substituted derivative is accessible by such a simple isolation process, it is usually used as scaffold for further derivatization.

Since the Diels-Alder reaction between a morphinan-6,8-diene and a dienophile affords almost exclusively the 7α-adduct, the isolation of the 7β-epimer (e.g. E or F) requires, compared to the isolation of the 7α-isomer (e.g. C or D), a much more elaborated purification process and affords the 7β-epimer only in a very low yield. For example, Diels-Alder reaction of methyl vinyl ketone with thebaine (B) afforded 7α-isomer D in 98% yield by simple filtration. From the filtrate, the 7β-isomer F was isolated by fractional crystallization in a total yield of 0.49% (Bentley et al., supra).

Also, Marton et al. (*Synth. Commun.* 25:829-848 (1995)) describe another example of the cumbersome purification process which describes the currently best-known protocol for the isolation of a β-isomer. In this process, starting from thebaine, the separation of the β-dihydrothevinone is reported in an overall yield of 0.92%.

It has now been discovered that 7β-substituted 6α,14α-ethenomorphinans and 7β-substituted 6α,14α-ethanomorphinans can easily be separated from an epimer mixture with the corresponding 7α-epimers in a simple process affording the 7β-epimers in about 98-100% purity and high recovery (from about 40% to over 80%).

Accordingly, the present disclosure provides a process for increasing the proportion of the 7β-epimer in an 7α/7β-epimer mixture of a 7-substituted 6α,14α-ethenomorphinan or a 7-substituted 6α,14α-ethanomorphinan, said process comprising: contacting a solution of the 7α/7β-epimer mixture with an acid to provide a precipitate, and isolating the precipitate to provide an isolated precipitate and a mother liquor.

In one embodiment, the process of the present invention increases the proportion of the 7β-epimer in an 7α/7β-epimer mixture of a compound of Formula I:

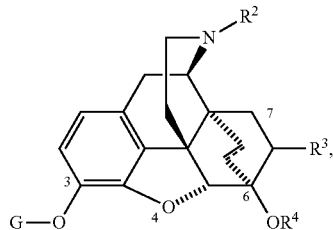

wherein:

G is $R^1$ or a hydroxyl protecting group PG;

$R^1$ is hydrogen, alkyl, alkenyl, alkynyl, (cycloalkyl)alkyl, (heterocyclo)alkyl, arylalkyl, or heteroarylalkyl, wherein the cycloalkyl, heterocyclo, aryl, and heteroaryl portions thereof are optionally substituted with 1, 2, or 3 substituents, each independently selected from the group consisting of hydroxy, alkyl, halo, haloalkyl, carboxy, alkoxy, alkylcarbonyl, and alkoxycarbonyl;

$R^2$ is (a) hydrogen, cyano, alkylcarbonyl, alkoxycarbonyl, or carboxamido; or (b) alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, alkoxy, alkylcarbonyl, and alkoxycarbonyl;

$R^3$ is selected from the group consisting of alkyl, alkenyl, alkynyl, cycloalkyl, cycloalkenyl, heterocyclo, aryl, heteroaryl, (cycloalkyl)alkyl, (cycloalkyl)alkenyl, (cycloalkenyl)alkyl, (cycloalkenyl)alkenyl, (heterocyclo)alkyl, (heterocyclo)alkenyl, arylalkyl, arylalkenyl, heteroarylalkyl, heteroarylalkenyl, alkylcarbonyl, (arylalkyl)carbonyl, formyl and cyano, wherein any of which, when other than formyl or cyano, is optionally substituted with 1, 2, or 3 substituents, each independently selected from the group consisting of hydroxy, alkyl, hydroxyalkyl, halo, haloalkyl, alkoxy, alkylcarbonyl, and alkoxycarbonyl;

$R^4$ is selected from the group consisting of hydrogen, alkyl, alkenyl, alkynyl, cycloalkyl, cycloalkenyl, heterocyclo, aryl, heteroaryl, (cycloalkyl)alkyl, (cycloalkyl)alkenyl, (cycloalkenyl)alkyl, (cycloalkenyl)alkenyl, (heterocyclo)alkyl, (heterocyclo)alkenyl, arylalkyl, arylalkenyl, heteroarylalkyl, and heteroarylalkenyl, wherein any of which, when other than hydrogen, is optionally substituted with 1, 2, or 3 substituents, each independently selected from the group consisting of hydroxy, alkyl, halo, haloalkyl, alkoxy, alkylcarbonyl, and alkoxycarbonyl; and ⫽ is a single bond or a double bond.

The 7β-epimer and the 7α-epimer of compounds of Formula I can be represented as Formulae $I^b$ and $I^a$, respectively:

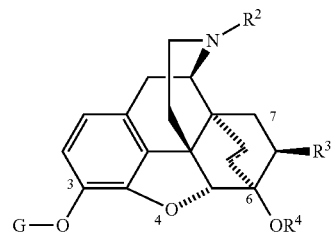

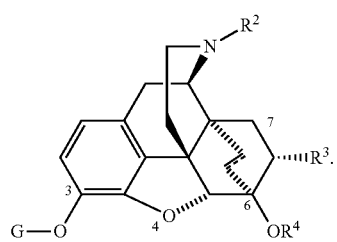

In another embodiment, the process of the present invention increases the proportion of the 7β-epimer in an 7α/7β-epimer mixture of a compound of Formula II:

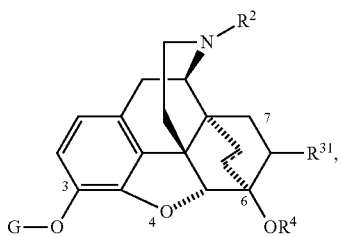

wherein:

G is $R^1$ or a hydroxyl protecting group PG;

$R^1$ is hydrogen, alkyl, alkenyl, alkynyl, (cycloalkyl)alkyl, (heterocyclo)alkyl, arylalkyl, or heteroarylalkyl, wherein the cycloalkyl, heterocyclo, aryl, and heteroaryl portions thereof are optionally substituted with 1, 2, or 3 substituents, each independently selected from the group consisting of hydroxy, alkyl, halo, haloalkyl, carboxy, alkoxy, alkylcarbonyl, and alkoxycarbonyl;

$R^2$ is (a) hydrogen, cyano, alkylcarbonyl, alkoxycarbonyl, or carboxamido; or (b) alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, alkoxy, alkylcarbonyl, and alkoxycarbonyl;

$R^{31}$ is selected from the group consisting of alkyl, alkenyl, alkynyl, cycloalkyl, cycloalkenyl, heterocyclo, aryl, heteroaryl, (cycloalkyl)alkyl, (cycloalkyl)alkenyl, (cycloalkenyl)alkyl, (cycloalkenyl)alkenyl, (heterocyclo)alkyl, (heterocyclo)alkenyl, arylalkyl, arylalkenyl, heteroarylalkyl, heteroarylalkenyl, alkylcarbonyl, (arylalkyl)carbonyl, and formyl, wherein any of which, when other than formyl, is optionally substituted with 1, 2, or 3 substituents, each independently selected from the group consisting of hydroxy, alkyl, hydroxyalkyl, halo, haloalkyl, alkoxy, alkylcarbonyl, and alkoxycarbonyl;

$R^4$ is selected from the group consisting of hydrogen, alkyl, alkenyl, alkynyl, cycloalkyl, cycloalkenyl, heterocyclo, aryl, heteroaryl, (cycloalkyl)alkyl, (cycloalkyl)alkenyl, (cycloalkenyl)alkyl, (cycloalkenyl)alkenyl, (heterocyclo)alkyl, (heterocyclo)alkenyl, arylalkyl, arylalkenyl, heteroarylalkyl, and heteroarylalkenyl, wherein any of which, when other than hydrogen, is optionally substituted with 1, 2, or 3 substituents, each independently selected from the group consisting of hydroxy, alkyl, halo, haloalkyl, alkoxy, alkylcarbonyl, and alkoxycarbonyl; and ⫽ is a single bond or a double bond.

In this aspect of the present invention, the isolated precipitate contains an increased proportion of the 7β-epimer as a salt relative to the 7α/7β-epimer mixture of a compound of Formula II. In one embodiment, the proportion of the 7β-epimer in the isolated precipitate is at least about 60%, at least about 70%, at least about 80%, or at least about 90%.

In another embodiment, the process of the present invention increases the proportion of the 7β-epimer in an 7α/7β-epimer mixture of a compound of Formula III:

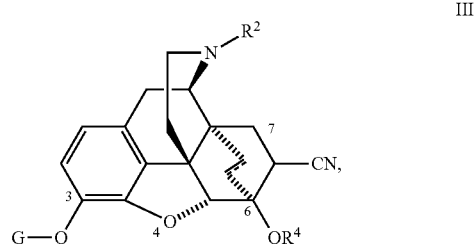

wherein:

G is $R^1$ or a hydroxyl protecting group PG;

$R^1$ is hydrogen, alkyl, alkenyl, alkynyl, (cycloalkyl)alkyl, (heterocyclo)alkyl, arylalkyl, or heteroarylalkyl, wherein the cycloalkyl, heterocyclo, aryl, and heteroaryl portions thereof are optionally substituted with 1, 2, or 3 substituents, each independently selected from the group consisting of hydroxy, alkyl, halo, haloalkyl, carboxy, alkoxy, alkylcarbonyl, and alkoxycarbonyl;

$R^2$ is (a) hydrogen, cyano, alkylcarbonyl, alkoxycarbonyl, or carboxamido; or (b) alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, alkoxy, alkylcarbonyl, and alkoxycarbonyl;

$R^4$ is selected from the group consisting of hydrogen, alkyl, alkenyl, alkynyl, cycloalkyl, cycloalkenyl, heterocyclo, aryl, heteroaryl, (cycloalkyl)alkyl, (cycloalkyl)alkenyl, (cycloalkenyl)alkyl, (cycloalkenyl)alkenyl, (heterocyclo)alkyl, (heterocyclo)alkenyl, arylalkyl, arylalkenyl, heteroarylalkyl, and heteroarylalkenyl, wherein any of which, when other than hydrogen, is optionally substituted with 1, 2, or 3 substituents, each independently selected from the group consisting of hydroxy, alkyl, halo, haloalkyl, alkoxy, alkylcarbonyl, and alkoxycarbonyl; and ⫽ is a single bond or a double bond.

In this aspect of the present invention, an increased proportion of the 7β-epimer salt, relative to the 7α/7β-epimer mixture of a compound of Formula III, can be found in the isolated precipitate or in the mother liquor depending on the conditions (i.e., the acid and/or the solvent) of the precipitation. In one embodiment, the isolated precipitate contains an increased proportion of the 7β-epimer as a salt relative to the 7α/7β-epimer mixture of a compound of Formula III. In this embodiment, the proportion of the 7β-epimer in the isolated precipitate is at least about 60%, at least about 70%, at least about 80%, or at least about 90%. In another embodiment, the mother liquor contains an increased proportion of the 7β-epimer as a salt relative to the 7α/7β-epimer mixture of a compound of Formula III. In this embodiment, the proportion of the 7β-epimer in the mother liquor is at least about 60%, at least about 70%, at least about 80%, or at least about 90%.

In another aspect, the present disclosure provides a process for purifying the 7β-epimer from an 7α/7β-epimer mixture of a 7-substituted 6α,14α-ethenomorphinan or a 7-substituted 6α,14α-ethanomorphinan. Said process comprises contacting a solution of the 7α/7β-epimer mixture with an acid under conditions conducive to precipitation of the 7β-epimer, and isolating the precipitate. In one embodiment, the proportion of the 7β-epimer as a salt in the isolated precipitate relative to the 7α/7β-epimer mixture is at least about 60%, at least about 70%, at least about 80%, or at least about 90%.

In one embodiment, the process comprises purifying the 7β-epimer from an 7α/7β-epimer mixture of a compound of Formula I.

In another embodiment, the process comprises purifying the 7β-epimer from an 7α/7β-epimer mixture of a compound of Formula II.

In another embodiment, the process comprises purifying the 7β-epimer from an 7α/7β-epimer mixture of a compound of Formula III.

The 7α/7β-epimer mixture used in the processes of the present invention can be, for example, the reaction mixture after the Diels-Alder reaction (e.g., the mother liquor obtained after the first precipitate is filtered off), the reaction mixture after further functionalization of the ketone group (e.g., after the reaction with a Grignard reagent), or the reaction mixture after the hydrogenation of the double bond. In one embodiment, the 7α/7β-epimer mixture used in the processes of the present invention is the product of the epimerization of the first precipitate or the mother liquor obtained after the salt formation. In one embodiment, prior to contacting with the acid, the reaction mixture is typically concentrated, and then any precipitation is dissolved by optionally adding a solvent and by heating to obtain a solution.

In another embodiment, the mother liquor is concentrated to dryness and the residue is redissolved in a solvent at an elevated temperature to obtain a solution before adding the acid.

In certain embodiments, the 7α/7β-epimer mixture can be an isolated precipitate that is further purified with respect to the 7β-epimer by the processes of the present invention. In this aspect of the invention, the 7α/7β-epimer mixture is first dissolved in a solvent at an elevated temperature to obtain a solution of the 7α/7β-epimer mixture before adding the acid.

In one embodiment, the solution of the 7α/7β-epimer mixture is contacted with the acid at about room temperature. In another embodiment, the solution of the 7α/7β-epimer mixture is contacted with the acid at about 50° C. to about the boiling point of the solution. Preferably, the temperature of the solution is from about 55° C. to the reflux temperature of the solvent, and more preferably the temperature of the solution is from about 60° C. to the reflux temperature of the solvent. In another embodiment, the temperature of the solution of the 7α/7β-epimer mixture is from about 55° C. to about 80° C., and more preferably the temperature is from about 60° C. to about 80° C.

Suitable solvents to be used in the process of the present invention include, for example, aliphatic alcohols, aromatic solvents, ethers (such as aliphatic ethers or THF), and acetonitrile, or combinations thereof. Typically, the solvent is an aliphatic alcohol, an aromatic solvent, and aliphatic ether, or combinations thereof.

In one embodiment, the solvent is an aliphatic alcohol or mixtures thereof. Suitable aliphatic alcohols include $C_{1-6}$ alcohols, such as methanol, ethanol, n-propanol, iso-propanol, n-butanol, n-pentanol, and n-hexanol, and preferably methanol, ethanol, n-propanol, and iso-propanol, and preferably iso-propanol.

In another embodiment, the solvent is an aromatic solvent. Suitable aromatic solvents include, for example, toluene, xylene and benzene, and preferably toluene.

In another embodiment, the solvent is an aliphatic ether. Suitable aliphatic ethers include, for example, $C_{5-6}$ cycloalkyl($C_{1-6}$)alkyl ethers, such as cyclopentyl methyl ether.

Typically, the solvent in the processes of the present invention is selected from the group consisting of methanol, ethanol, n-propanol, iso-propanol, toluene, and cyclopropyl methyl ether, or the solvent can be a combination (i.e., a mixture) of these solvents.

The solution of the 7α/7β-epimer mixture is contacted with the acid either at the elevated temperature or after cooling it, for example, to room temperature. Typically, the solution of the 7α/7β-epimer mixture is contacted with the acid at an elevated temperature and then the mixture is cooled to form a precipitate. The solution of the 7α/7β-epimer mixture is contacted with the acid, for example, by simply adding, preferably portion wise (or dropwise when dissolved in a suitable solvent), a sufficient amount of the acid to the solution and mixing. The sufficient amount of the acid is an amount that is necessary for converting the 7β-epimer of the 7α/7β-epimer mixture into its salt. In one embodiment, the amount of the acid is from about 0.5 to about 1.5 equivalents based on the amount of the 7β-epimer. In another embodiment, the amount of the acid is from about 0.8 to about 1.3 equivalents, preferably from about 0.9 to about 1.2 equivalents, and more preferably about 1.0 or about 1.1 equivalents based on the amount of the 7β-epimer. The amount of the 7β-epimer of the 7-substituted 6α,14α-ethenomorphinan or the 7-substituted 6α,14α-ethanomorphinan can be determined by conventional methods described in the art, such as, for example by $^1$H NMR: interation of the H-5 protons, as described in Uff et al., *Magnetic Resonance in Chemistry* 23:6 (1985); Marton, J., et al., *Acta Chemica Scandinavia* 52:1234-1238 (1998); and Derrick, I., et al., *Tetrahedron Letters* 41:7571-7576 (2000), and by HPLC as described in the examples.

In one embodiment, the proportion of the 7β-epimer in the 7α/7β-epimer mixture is at least about 20%. In another embodiment, the proportion of the 7β-epimer in the 7α/7β-epimer mixture is at least about 50%.

In one embodiment the acid is an achiral acid. In another embodiment, the acid is a chiral acid.

In one embodiment, the acid is selected from the group consisting of an aliphatic monocarboxylic acid and an aliphatic dicarboxylic acid, or a combination thereof, any of which is optionally substituted. In another embodiment, the acid is an optionally substituted, saturated or unsaturated aliphatic monocarboxylic acid, and preferably a saturated or unsaturated $C_{1-6}$ aliphatic monocarboxylic acid optionally substituted with 1, 2, or 3 substituents, each independently selected from the group consisting of halogen and hydroxy. Typically, in this aspect of the invention, the acid is a saturated, unsubstituted $C_{1-4}$ aliphatic monocarboxylic acid, or a saturated $C_{1-4}$ aliphatic monocarboxylic acid substituted with 1, 2 or 3 substituents, each independently selected from the group consisting of fluoro, chloro, bromo, iodo, and hydroxy. Advantageously, the monocarboxylic acid is selected from the group consisting of acetic acid, trifluoroacetic acid (TFA), trichloroacetic acid, and tribromoacetic acid, and preferably TFA.

In another embodiment, the acid is an optionally substituted, saturated or unsaturated aliphatic dicarboxylic acid, and preferably a saturated $C_{2-6}$ aliphatic dicarboxylic acid optionally substituted with 1, 2, or 3 substituents, each independently selected from the group consisting of halogen and hydroxy. Typically, in this aspect of the invention, the acid is an unsaturated $C_{2-6}$ aliphatic dicarboxylic acid optionally substituted with 1, 2, or 3 substituents, each independently selected from the group consisting of halogen and hydroxy, and preferably an unsaturated, unsubstituted $C_{2-6}$ aliphatic dicarboxylic acid. Advantageously, the dicarboxylic acid is fumaric acid or maleic acid.

The precipitate can be isolated by any conventional separation process. Suitable separation processes for isolating the precipitate include, for example, filtration, such as vacuum filtration, and centrifugal separations. Preferably, the precipitate is isolated by filtration, and the filter cake is optionally washed to remove any residual mother liquor.

In another embodiment, G in compounds of any of Formulae I-III is $R^1$.

In another embodiment, $R^1$ is hydrogen.

In another embodiment, $R^1$ is alkyl, alkenyl, or alkynyl, and specifically $C_{1-4}$ alkyl, $C_{2-4}$ alkenyl, or $C_{2-4}$ alkynyl. In another embodiment, $R^1$ is methyl, ethyl, n-propyl, iso-propyl, n-butyl, tert-butyl, iso-butyl, or sec-butyl, and advantageously $R^1$ is methyl. In another embodiment, $R^1$ is ethenyl, propenyl, isopropenyl, butenyl, or sec-butenyl. In another embodiment, $R^1$ is ethynyl, propynyl, butynyl, or 2-butynyl.

In another embodiment, $R^1$ is (cycloalkyl)alkyl, (heterocyclo)alkyl, arylalkyl, or heteroarylalkyl, wherein the cycloalkyl, heterocyclo, aryl, or heteroaryl portions thereof are optionally substituted with 1, 2 or 3 substituents, each independently selected from the group consisting of hydroxy, alkyl, halo, haloalkyl, carboxy, alkoxy, alkylcarbonyl, and alkoxycarbonyl.

Suitable (cycloalkyl)alkyl groups for $R^1$ include $C_{3-7}$ cycloalkyl($C_{1-4}$)alkyl groups, and specifically $C_{3-6}$ cycloalkyl($C_{1-4}$)alkyl groups, wherein the cycloalkyl portion is optionally substituted with 1, 2, or 3 substituents, each independently selected from the group consisting of hydroxy, alkyl, halo, haloalkyl, carboxy, alkoxy, alkylcarbonyl, and alkoxycarbonyl. In another embodiment, $R^1$ is cyclopropyl($C_{1-4}$)alkyl, cyclobutyl($C_{1-4}$)alkyl, cyclopentyl ($C_{1-4}$)alkyl, or cyclohexyl($C_{1-4}$)alkyl, optionally substituted with 1 or 2 substituents, each independently selected from the group consisting of hydroxy, $C_{1-4}$ alkyl, halo, halo ($C_{1-4}$)alkyl, carboxy, $C_{1-4}$ alkoxy, $C_{1-4}$ alkylcarbonyl, and $C_{1-4}$ alkoxycarbonyl. In another embodiment, $R^1$ is unsubstituted (cyclopropyl)methyl, 2-(cyclopropyl)ethyl or 3-(cyclopropyl)propyl.

Suitable (heterocyclo)alkyl groups for $R^1$ include 5- or 6-membered heterocyclo($C_{1-4}$)alkyl, wherein the heterocyclo portion is optionally substituted with 1, 2, or 3 substituents each independently selected from the group consisting of hydroxy, alkyl, halo, haloalkyl, carboxy, alkoxy, alkylcarbonyl, and alkoxycarbonyl; and typically optionally substituted with 1 or 2 substituents, each independently selected from the group consisting of hydroxy, $C_{1-4}$ alkyl, halo, halo($C_{1-4}$)alkyl, carboxy, $C_{1-4}$ alkoxy, $C_{1-4}$ alkylcarbonyl, and $C_{1-4}$ alkoxycarbonyl. In another embodiment, $R^1$ is unsubstituted 5- or 6-membered heterocyclo($C_{1-4}$)alkyl, such as tetrahydrofuranyl($C_{1-4}$)alkyl.

Suitable arylalkyl groups for $R^1$ include aryl($C_{1-4}$)alkyl groups wherein the aryl portion is optionally substituted with 1, 2, or 3 substituents, each independently selected from the group consisting of hydroxy, alkyl, halo, haloalkyl, carboxy, alkoxy, alkylcarbonyl, and alkoxycarbonyl; and typically optionally substituted with 1 or 2 substituents, each independently selected from the group consisting of hydroxy, $C_{1-4}$ alkyl, halo, halo($C_{1-4}$)alkyl, carboxy, $C_{1-4}$ alkoxy, $C_{1-4}$ alkylcarbonyl, and $C_{1-4}$ alkoxycarbonyl. In another embodiment, $R^1$ is $C_{6-10}$ aryl($C_{1-4}$)alkyl substituted with one or two substituents, each independently selected from the group consisting of hydroxy, $C_{1-4}$ alkyl, halo, halo($C_{1-4}$)alkyl, carboxy, $C_{1-4}$ alkoxy, $C_{1-4}$ alkylcarbonyl, and $C_{1-4}$ alkoxycarbonyl. In another embodiment, $R^1$ is benzyl, phenethyl, or naphthylmethyl substituted with 1 or 2 substituents, each independently selected from the group consisting of hydroxy, methyl, ethyl, fluorine, bromine, iodine, chlorine, trifluoromethyl, carboxy, methoxy, ethoxy, methylcarbonyl, ethylcarbonyl, methoxycarbonyl, and ethoxycarbonyl. In another embodiment, $R^1$ is unsubstituted $C_{6-10}$ aryl($C_{1-4}$)alkyl, such as benzyl, phenethyl, 3-phenylpropyl, 4-phenylbutyl, naphthylmethyl, 2-naphthylethyl, 3-naphthylpropyl, and 4-naphthylbutyl; typically benzyl and phenethyl, and especially benzyl.

Suitable heteroarylalkyl groups for $R^1$ include heteroaryl($C_{1-4}$)alkyl groups wherein the heteroaryl portion is optionally substituted with 1, 2, or 3 substituents, each independently selected from the group consisting of hydroxy, alkyl, halo, haloalkyl, carboxy, alkoxy, alkylcarbonyl, and alkoxycarbonyl; and typically optionally substituted with 1 or 2 substituents, each independently selected from the group consisting of hydroxy, $C_{1-4}$ alkyl, halo, halo($C_{1-4}$)alkyl, carboxy, $C_{1-4}$ alkoxy, $C_{1-4}$ alkylcarbonyl, and $C_{1-4}$ alkoxycarbonyl. In another embodiment, $R^1$ is 5- or 6-membered heteroaryl($C_{1-4}$)alkyl, such as furanyl($C_{1-4}$)alkyl, substituted with 1 or 2 substituents, each independently selected from the group consisting of hydroxy, $C_{1-4}$ alkyl, halo, halo($C_{1-4}$)alkyl, carboxy, $C_{1-4}$ alkoxy, $C_{1-4}$ alkylcarbonyl, and $C_{1-4}$ alkoxycarbonyl; and typically each independently selected from the group consisting of hydroxy, halo, halo($C_{1-2}$)alkyl, carboxy, $C_{1-2}$ alkoxy, $C_{1-2}$ alkylcarbonyl, and $C_{1-2}$ alkoxycarbonyl.

In another embodiment, $R^2$ in compounds of any of Formulae I-III is hydrogen, cyano, alkylcarbonyl, alkoxycarbonyl, or carboxamido. In this aspect of the invention, typically $R^2$ is hydrogen, cyano, $C_{1-4}$ alkylcarbonyl, $C_{1-4}$ alkoxycarbonyl, —CONH$_2$, —CON(H)C$_{1-4}$ alkyl, —CON(C$_{1-4}$ alkyl)$_2$, or —CON(H)Ph.

In another embodiment, $R^2$ is alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, alkoxy, alkylcarbonyl, and alkoxycarbonyl. Useful compounds include those where $R^2$ is $C_{1-6}$ alkyl, $C_{2-6}$ alkenyl, $C_{2-6}$ alkynyl, $C_{3-7}$ cycloalkyl, $C_{3-7}$ cycloalkenyl, 5- or 6-membered heterocyclo, aryl, 5- or 6-membered heteroaryl, $C_{3-7}$ cycloalkyl($C_{1-4}$)alkyl, $C_{3-7}$ cycloalkenyl($C_{1-4}$)alkyl, 5- or 6-membered heterocyclo($C_{1-4}$)alkyl, aryl($C_{1-4}$)alkyl, 5- or 6-membered heteroaryl($C_{1-4}$)alkyl, aryl($C_{1-4}$)alkoxycarbonyl, or 5- or 6-membered heteroaryl($C_{1-4}$)alkoxycarbonyl, any of which is optionally substituted with 1, 2, or 3 substituents, each independently selected from the group consisting of hydroxy, alkyl, halo, haloalkyl, alkoxy, alkylcarbonyl, and alkoxycarbonyl. In another embodiment, $R^2$ is $C_{1-6}$ alkyl, $C_{2-6}$ alkenyl, $C_{2-6}$ alkynyl, $C_{3-7}$ cycloalkyl, $C_{3-7}$ cycloalkenyl, 5- or 6-membered heterocyclo, $C_{6-10}$ aryl, 5- or 6-membered heteroaryl, $C_{3-7}$ (cycloalkyl)($C_{1-4}$)alkyl, $C_{3-7}$ (cycloalkenyl)($C_{1-4}$)alkyl, 5- or 6-membered heterocyclo($C_{1-4}$)alkyl, $C_{6-10}$ aryl($C_{1-4}$)alkyl, 5- or 6-membered heteroaryl($C_{1-4}$)alkyl, $C_{6-10}$ aryl($C_{1-4}$)alkoxycarbonyl, or 5- or 6-membered heteroaryl($C_{1-4}$)alkoxycarbonyl, any of which is optionally substituted with 1, 2, or 3 substituents, each independently selected from the group consisting of hydroxy, $C_{1-4}$ alkyl, halo, halo($C_{1-4}$)alkyl, $C_{1-4}$ alkoxy, $C_{1-4}$ alkylcarbonyl, and $C_{1-4}$ alkoxycarbonyl, and especially optionally substituted with 1 or 2 substituents, each independently selected from the group consisting of hydroxy, methyl, ethyl, halo, trifluoromethyl, methoxy, ethoxy, methylcarbonyl, ethylcarbonyl, methoxycarbonyl, and ethoxycarbonyl. In another embodiment, $R^2$ is $C_{3-7}$ (cycloalkyl)($C_{1-4}$)alkyl or $C_{3-7}$ (cycloalkenyl)($C_{1-4}$)alkyl, and especially $C_{3-7}$ (cycloalkyl)($C_{1-4}$)alkyl, such as cyclopropyl($C_{1-4}$)alkyl, cyclobutyl($C_{1-4}$)alkyl, cyclopentyl($C_{1-4}$)alkyl, or cyclohexyl($C_{1-4}$)alkyl, optionally substituted with 1, 2, or 3 substituents, each independently selected from the group consisting of hydroxy, $C_{1-4}$ alkyl, halo, halo($C_{1-4}$)alkyl, $C_{1-4}$ alkoxy, $C_{1-4}$ alkylcarbonyl, and $C_{1-4}$ alkoxycarbonyl, and especially optionally substituted with 1 or 2 substituents, each independently selected from the group consisting of hydroxy, methyl, ethyl, halo, trifluoromethyl, methoxy, ethoxy, methylcarbonyl, ethylcarbonyl, methoxycarbonyl, and ethoxycarbonyl. In another embodiment, $R^2$ is unsubstituted (cyclopropyl)methyl, 2-(cyclopropyl)ethyl or 3-(cyclopropyl)propyl.

In another embodiment, $R^3$ in compounds of Formula I or $R^{31}$ in compounds of Formula II is selected from the group consisting of $C_{1-6}$ alkyl, $C_{2-6}$ alkenyl, $C_{2-6}$ alkynyl, $C_{3-7}$ cycloalkyl, $C_{3-7}$ cycloalkenyl, 5- to 6-membered heterocyclo, $C_{6-12}$ aryl, 5- to 10-membered heteroaryl, $C_{3-7}$ cycloalkyl($C_{1-6}$)alkyl, $C_{3-7}$ cycloalkyl($C_{2-6}$)alkenyl, $C_{3-7}$ cycloalkenyl($C_{1-6}$)alkyl, $C_{3-7}$ cycloalkenyl($C_{2-6}$)alkenyl, 5- to 6-membered heterocyclo($C_{1-4}$)alkyl, 5- to 6-membered heterocyclo($C_{2-4}$)alkenyl, $C_{6-12}$ aryl($C_{1-6}$)alkyl, $C_{6-12}$ aryl($C_{2-6}$)alkenyl, 5- to 10-membered heteroaryl($C_{1-4}$)alkyl, 5- to 10-membered heteroaryl($C_{2-6}$)alkenyl, $C_{1-6}$ alkylcarbonyl, ($C_{6-12}$ aryl($C_{1-4}$)alkyl)carbonyl, and formyl, wherein any of which, when other than formyl, is optionally substituted with 1, 2, or 3 substituents, each independently selected from the group consisting of hydroxy, alkyl, hydroxy($C_{1-6}$)alkyl, halo, halo($C_{1-5}$)alkyl, $C_{1-6}$ alkoxy, $C_{1-6}$ alkylcarbonyl, and $C_{1-6}$ alkoxycarbonyl. In another embodiment, $R^3$ is $C_{1-6}$ alkylcarbonyl, which is unsubstituted or substituted with 1, 2, or 3 substituents, each independently selected from the group consisting of hydroxy, alkyl, hydroxy($C_{1-6}$)alkyl, halo, halo($C_{1-6}$)alkyl, $C_{1-6}$ alkoxy, $C_{1-6}$ alkylcarbonyl, and $C_{1-6}$ alkoxycarbonyl.

In another embodiment, $R^4$ in compounds of any of Formulae I-III is selected from the group consisting of hydrogen, $C_{1-6}$ alkyl, $C_{2-6}$ alkenyl, $C_{2-6}$ alkynyl, $C_{3-7}$ cycloalkyl, $C_{3-7}$ cycloalkenyl, 5- to 6-membered heterocyclo, $C_{6-12}$ aryl, 5- to 10-membered heteroaryl, $C_{3-7}$ cycloalkyl($C_{1-6}$)alkyl, $C_{3-7}$ cycloalkyl($C_{2-6}$)alkenyl, $C_{3-7}$ cycloalkenyl($C_{1-6}$)alkyl, $C_{3-7}$ cycloalkenyl($C_{2-6}$)alkenyl, 5- to 6-membered heterocyclo($C_{1-4}$)alkyl, 5- to 6-membered heterocyclo($C_{2-6}$)alkenyl, $C_{6-12}$ aryl($C_{1-6}$)alkyl, $C_{6-12}$ aryl($C_{2-6}$)alkenyl, 5- to 10-membered heteroaryl($C_{1-6}$)alkyl, and 5- to 10-membered heteroaryl($C_{1-6}$)alkenyl, wherein any of which, when other than hydrogen, is optionally substituted with 1, 2, or 3 substituents, each independently selected from the group consisting of hydroxy, $C_{1-6}$ alkyl, halo, halo($C_{1-6}$)alkyl, $C_{1-6}$ alkoxy, $C_{1-6}$ alkylcarbonyl, and $C_{1-6}$ alkoxycarbonyl. Typically, $R^4$ is hydrogen or unsubstituted $C_{1-6}$ alkyl.

In another embodiment, ⫽ is a single bond in compounds of any of Formulae I-III.

In another embodiment, ⫽ is a double bond in compounds of any of Formulae I-III.

In another embodiment, the 7β-epimer of compounds of any of Formulae I-II is represented by Formula IV:

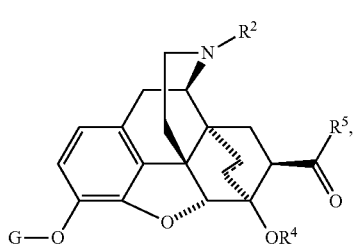

IV wherein $R^1$, $R^2$, $R^4$, G, and ⫽ are as defined above for Formula I, and $R^5$ is H or $C_{1-6}$ alkyl, which is unsubstituted or substituted with 1, 2, or 3 substituents, each independently selected from the group consisting of hydroxy, hydroxy($C_{1-4}$)alkyl, halo, halo($C_{1-4}$)alkyl, $C_{1-6}$ alkoxy, $C_{1-6}$ alkylcarbonyl, and $C_{1-6}$ alkoxycarbonyl.

In another embodiment, the 7α/7β-epimer mixture of a compound of Formula I is represented by Formula V:

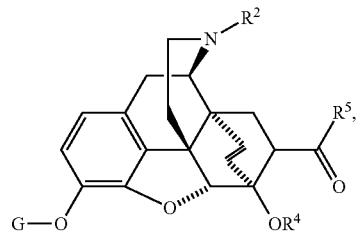

V wherein
$R^1$, $R^2$, $R^4$, and G are as defined above for Formula I, and $R^5$ is $C_{1-6}$ alkyl, which is unsubstituted or substituted with 1, 2, or 3 substituents, each independently selected form the group consisting of hydroxy, hydroxy($C_{1-4}$)alkyl, halo, halo($C_{1-4}$)alkyl, $C_{1-4}$ alkoxy, $C_{1-4}$ alkylcarbonyl, and $C_{1-4}$ alkoxycarbonyl.

In another embodiment, in compounds of any of Formulae I-V, $R^1$ is hydrogen, $C_{1-6}$ alkyl, or benzyl; $R^2$ is $C_{2-6}$ alkenyl, cyclopropyl($C_{1-4}$)alkyl, cyclobutyl($C_{1-4}$)alkyl, cyclopentyl($C_{1-4}$)alkyl, or cyclohexyl($C_{1-4}$)alkyl, optionally substituted with 1, 2, or 3 substituents, each independently selected from the group consisting of hydroxy, $C_{1-4}$ alkyl, halo, halo($C_{1-4}$)alkyl, $C_{1-4}$ alkoxy, $C_{1-4}$ alkylcarbonyl, and $C_{1-4}$ alkoxycarbonyl; and $R^4$ is hydrogen or $C_{1-6}$ alkyl. In another embodiment, $R^2$ is unsubstituted $C_{2-6}$ alkenyl or unsubstituted cyclopropyl($C_{1-4}$)alkyl. In another embodiment, $R^2$ is (cyclopropyl)methyl. In another embodiment, $R^1$ is hydrogen, $C_{1-6}$ alkyl, or benzyl. In another embodiment, $R^2$ is (cyclopropyl)methyl.

In another embodiment, G in compounds of any of Formulae I-V is a hydroxyl protecting group PG.

Suitable hydroxyl protecting groups for PG are well known and include, for example, any suitable hydroxyl protecting group disclosed in Wuts, P. G. M. & Greene, T. W., Greene's Protective Groups in Organic Synthesis, 4rd Ed., pp. 16-430 (J. Wiley & Sons, 2007), herein incorporated by reference in its entirety. The term "hydroxyl protecting group" as used herein refers to group that blocks (i.e., protects) the hydroxy functionality while reactions are carried out on other functional groups or parts of the molecule. Those skilled in the art will be familiar with the selection, attachment, and cleavage of protecting groups and will appreciate that many different protective groups are known in the art, the suitability of one protective group or another being dependent on the particular the synthetic scheme planned. Suitable hydroxyl protecting groups are generally able to be selectively introduced and removed using mild reaction conditions that do not interfere with other portions of the subject compounds. These protecting groups can be introduced or removed at a convenient stage using methods known in the art. The chemical properties of such groups, methods for their introduction and removal are known in the art and can be found, for example, in Greene, T. W. and Wuts, P. G. M., above. Additional hydroxy protecting groups can be found, for example, in U.S. Pat. No. 5,952,495, U.S. Patent Appl. Pub. No. 2008/0312411, WO 2006/035195, and WO 98/02033, herein incorporated in their entirety. Suitable hydroxyl protecting groups include the methoxymethyl, tetrahydropyranyl, tert-butyl, allyl, tert-butyldimethylsilyl, tert-butyldiphenylsilyl, acetyl, pivaloyl, benzoyl, benzyl (Bn), and p-methoxybenzyl group.

It is apparent to a person of ordinary skill in the art that certain groups included in the definitions of $R^1$ and PG are overlapping, such as tert-butyl, benzyl, etc., and, thus, certain compounds of Formulae I-V having $R^1$ groups that act as hydroxyl protecting groups can be pharmaceutically active.

In one embodiment, the hydroxyl protecting group PG is selected from the group consisting of alkyl, arylalkyl, heterocyclo, (heterocyclo)alkyl, acyl, silyl, and carbonate, any of which are optionally substituted.

In another embodiment, the hydroxyl protecting group is an alkyl group, typically an optionally substituted $C_{1-6}$ alkyl group, and suitably unsubstituted methyl or tert-butyl.

In another embodiment, the hydroxyl protecting group PG is an arylalkyl group. Suitable arylalkyl groups include, for example, an unsubstituted benzyl group, substituted benzyl groups, such as p-methoxybenzyl, and naphthylmethyl.

In another embodiment, the hydroxyl protecting group PG is a heterocyclo group, such as unsubstituted tetrahydropyranyl or optionally substituted tetrahydropyranyl.

In another embodiment, the hydroxyl protecting group PG is a silyl group. The term "silyl" as employed herein refers to the following group having the structure:

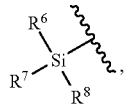

wherein $R^6$, $R^7$, and $R^8$ are each independently selected from the group consisting of alkyl, cycloalkyl, aryl, (cycloalkyl) alkyl, or arylalkyl, any of which is optionally substituted. In one embodiment, the silyl group is trimethyl silyl, tert-butyldimethyl silyl, tert-butyldiphenyl silyl, or tri-isopropyl silyl.

In another embodiment, the hydroxyl protecting group PG is an acyl group. The term "acyl" as employed herein refers to the following structure:

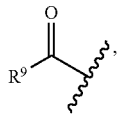

wherein $R^9$ is alkyl, cycloalkyl, aryl, (cycloalkyl)alkyl, or arylalkyl, any of which is optionally substituted. The acyl group can be, for example, $C_{1-4}$ alkylcarbonyl (such as, for example, acetyl), arylcarbonyl (such as, for example, benzoyl), levulinoyl, or pivaloyl. In another embodiment, the acyl group is benzoyl.

In another embodiment, the hydroxyl protecting group is a carbonate group. The term "carbonate" as employed herein refers to the following structure:

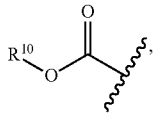

wherein $R^{10}$ is alkyl, alkenyl, cycloalkyl, aryl, (cycloalkyl)alkyl, or arylalkyl, any of which is optionally substituted. Typically, $R^{10}$ is $C_{1-10}$ alkyl (e.g., 2,4-dimethylpent-3-yl), $C_{2-6}$ alkenyl (e.g., ethenyl or prop-2-enyl, i.e., allyl), $C_{3-12}$ cycloalkyl (e.g., adamantyl), phenyl, or benzyl.

In another embodiment, the hydroxyl protecting group is a carbamate group. The term "carbamate" as employed herein refers to the following structure:

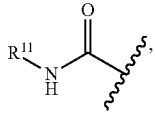

wherein $R^{11}$ is alkyl, alkenyl, cycloalkyl, aryl, (cycloalkyl)alkyl, or arylalkyl, any of which is optionally substituted. Typically, $R^{11}$ is $C_{1-10}$ alkyl (e.g., tert-butyl, 2,4-dimethylpent-3-yl), $C_{2-6}$ alkenyl (e.g., ethenyl or prop-2-enyl, i.e., allyl), $C_{3-12}$ cycloalkyl (e.g., adamantyl), phenyl, or benzyl.

The present invention also pertains to the preparation of 7β-substituted compounds of Formula $I^b$:

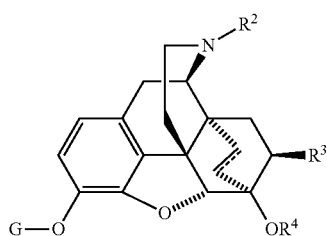

and the salts thereof, wherein
G and $R^2$-$R^4$ are as defined above for Formula I, comprising:

a) conducting a Diels-Alder reaction between a compound of Formula VI:

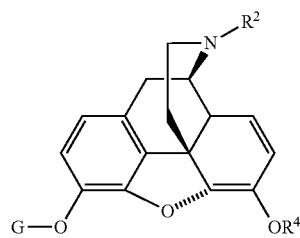

wherein G and $R^2$ are as defined above for Formula I, and a compound selected from the group consisting of:

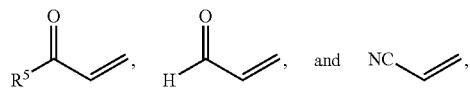

wherein $R^5$ is as defined above for Formula IV, to form a 7α/7β-epimer mixture of the compound of Formula I, where ⫽ is a double bond;

b) forming a first precipitate of the 7α/7β-epimer mixture;

c) isolating the first precipitate from the reaction mixture to obtain a first mother liquor;

d) optionally reducing the volume of the first mother liquor, and contacting the first mother liquor with an acid to provide a second precipitate;

e) isolating the second precipitate to obtain the compound of Formula $I^b$ as a salt, wherein ⫽ is a double bond, and a second mother liquor;

f) optionally converting the salt into its free base; and g) optionally hydrogenating the double bond to obtain a compound of Formula $I^b$, wherein ⫽ is a single bond.

The second mother liquor and/or the first precipitate are optionally epimerized and processed according to step d) above.

The present invention also pertains to the preparation of 7β-substituted compounds of Formula $V^b$:

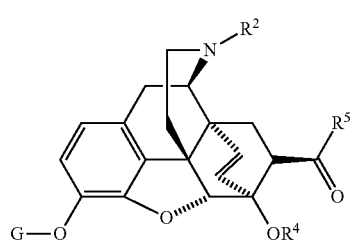

and the salts thereof, wherein
G is $R^1$ or a hydroxyl protecting group PG;
$R^1$ is hydrogen, alkyl, alkenyl, alkynyl, (cycloalkyl)alkyl, (heterocyclo)alkyl, arylalkyl, or heteroarylalkyl, wherein the cycloalkyl, heterocyclo, aryl, and heteroaryl portions thereof are optionally substituted with 1, 2, or 3 substituents, each independently selected from the group consisting of hydroxy, alkyl, halo, haloalkyl, carboxy, alkoxy, alkylcarbonyl, and alkoxycarbonyl;

$R^2$ is (a) hydrogen, cyano, alkylcarbonyl, alkoxycarbonyl, or carboxamido; or (b) alkyl, alkenyl, alkynyl, cycloalkyl, cycloalkenyl, heterocyclo, aryl, heteroaryl, (cycloalkyl)alkyl, (cycloalkenyl)alkyl, (heterocyclo)alkyl, arylalkyl, heteroarylalkyl, (arylalkoxy)carbonyl, or (heteroarylalkoxy)carbonyl, any of which is optionally substituted with 1, 2, or 3 substituents, each independently selected from the group consisting of hydroxy, alkyl, halo, haloalkyl, alkoxy, alkylcarbonyl, and alkoxycarbonyl;

$R^4$ is selected from the group consisting of hydrogen, alkyl, alkenyl, alkynyl, cycloalkyl, cycloalkenyl, heterocyclo, aryl, heteroaryl, (cycloalkyl)alkyl, (cycloalkyl)alkenyl, (cycloalkenyl)alkyl, (cycloalkenyl)alkenyl, (heterocyclo)alkyl, (heterocyclo)alkenyl, arylalkyl, arylalkenyl, heteroarylalkyl, and heteroarylalkenyl, wherein any of which, when other than hydrogen, is optionally substituted with 1, 2, or 3 substituents, each independently selected from the group consisting of hydroxy, alkyl, halo, haloalkyl, alkoxy, alkylcarbonyl, and alkoxycarbonyl; and $R^5$ is $C_{1-6}$ alkyl, which is unsubstituted or substituted with 1, 2, or 3 substituents, each independently selected from the group consisting of hydroxy, hydroxy($C_{1-4}$)alkyl, halo, halo($C_{1-4}$)alkyl, $C_{1-4}$ alkylcarbonyl, and $C_{1-4}$ alkoxycarbonyl, comprising:

a) conducting a Diels-Alder reaction between a compound of Formula VI:

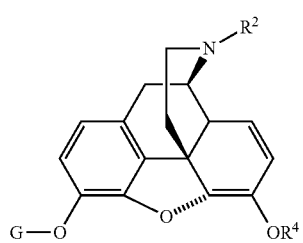

VI wherein G, $R^2$, and $R^4$ are as defined above, and a compound of Formula VII:

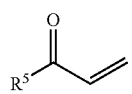

VII wherein $R^5$ is as defined above, to form a 7α/7β-epimer mixture of the compound of Formula V;

b) forming a first precipitate of the 7α/7β-epimer mixture;

c) isolating the first precipitate from the reaction mixture to obtain a first mother liquor;

d) optionally reducing the volume of the first mother liquor, and contacting the first mother liquor with an acid to provide a second precipitate;

e) isolating the second precipitate to obtain the compound of Formula $V^b$ as a salt, and a second mother liquor; and f) optionally converting the salt into its free base.

In one embodiment, the proportion of the 7β-epimer in the first mother liquor obtained from the Diels-Alder reaction is at least about 10%, at least about 15%, at least about 20%, or at least about 25%.

The first precipitate typically forms upon cooling the Diels-Alder reaction mixture and contains the 7α-epimer as the major product. The first precipitate can be isolated by, e.g., filtration, such as vacuum filtration, or centrifugal separators. Typically, the first mother liquor is partially concentrated, e.g., by evaporation, after the isolation of the first precipitate of the 7α/7β-epimer mixture. Then preferably, the first mother liquor is heated to dissolve any precipitate of the 7α/7β-epimer mixture and to obtain a solution containing the 7α/7β-epimer mixture. Optionally one or more additional solvents can be added to the first mother liquor. In another embodiment, the first mother liquor is concentrated to dryness and the residue is redissolved in a solvent to obtain a solution. Useful solvents are those described above in connection with Formula I, and are typically selected from the group consisting of aliphatic alcohols, aromatic solvents, aliphatic ethers, and combination's thereof. Preferably, the solvent is iso-propanol (IPA). Typically, the partially concentrated first mother liquor including the optional additional solvent, or the solution obtained from the residue, are heated to a temperature of about 50° C. to about the boiling point of the solution. Preferably, the temperature is from about 55° C. to the reflux temperature of the solvent, and more preferably the temperature is from about 60° C. to the reflux temperature of the solvent. In another embodiment, the temperature is from about 55° C. to about 80° C., and more preferably the temperature is from about 60° C. to about 80° C. The term "solvent" herein, includes mixtures/combinations of one or more solvents.

The heated first mother liquor is then contacted with an acid to obtain a second precipitate. In another embodiment, the heated mother liquor is first cooled down, for example to room temperature, and then contacted with the acid to obtain the second precipitate. Suitable and preferable acids are those described above in connection with the processes for increasing the proportion of the 7β-epimer and purifying the 7β-epimer. In one embodiment, the acid is TFA. In another embodiment, the amount of the acid used is from about 0.5 to about 1.5 equivalents based on the amount of the 7β-epimer. In another embodiment, the acid is used in an amount of from about 0.8 to about 1.3 equivalents, preferably from about 0.9 to about 1.2 equivalents, and more preferably about 1.0 or about 1.1 equivalents based on the amount of the 7β-epimer.

The second precipitate can be isolated by, e.g., vacuum filtration or centrifugal separators. In one embodiment, the proportion of the 7β-epimer in the second precipitate is at least about 60%, at least about 70%, at least about 80%, or at least about 90%.

The salts formed in the processes of the present invention can be converted to their free bases by methods known in the art and by the methods described in the examples.

The mother liquor obtained after isolating the second precipitate (the second mother liquor) is enriched with the 7α-epimer, which can be epimerized, for example, by reacting with potassium carbonate ($K_2CO_3$) or diazabicycloundec-7-ene (DBU), and then repeating the process as described above to obtain a further second precipitate of the 7β-epimer. The epimerization can be conducted, for example, as described by Marton, J., et al., *Acta Chemica Scandinavia* 52:1234-1238 (1998), and Derrick, I., et al., *Tetrahedron Letters* 41:7571-7576 (2000).

The first precipitate is also enriched with the 7α-epimer. This can be epimerized as described above by reacting with, for example, potassium carbonate ($K_2CO_3$) or diazabicycloundec-7-ene (DBU), and then repeating the process as described above to obtain a further second precipitate of the 7β-epimer.

Optional substituents attached to aryl, phenyl and heteroaryl rings each take the place of a hydrogen atom that would otherwise be present in any position on the aryl, phenyl or heteroaryl rings.

Useful halo or halogen groups include fluorine, chlorine, bromine and iodine.

Useful alkyl groups are selected from straight-chain and branched-chain $C_{1-10}$ alkyl groups. Typical $C_{1-10}$ alkyl groups include methyl, ethyl, propyl, isopropyl, butyl, sec-butyl, tert-butyl, iso-butyl, pentyl, 3-pentyl, hexyl, heptyl, octyl, nonyl and decyl, among others. In one embodiment, useful alkyl groups are selected from straight chain $C_{1-6}$ alkyl groups and branched chain $C_{3-6}$ alkyl groups. Typical $C_{1-6}$ alkyl groups include methyl, ethyl, propyl, isopropyl, butyl, sec-butyl, tert-butyl, iso-butyl, pentyl, 3-pentyl, hexyl, among others. In one embodiment, useful alkyl groups are selected from straight chain $C_{2-6}$ alkyl groups and branched chain $C_{3-6}$ alkyl groups. Typical $C_{2-6}$ alkyl groups include ethyl, propyl, isopropyl, butyl, sec-butyl, tert-butyl, iso-butyl, pentyl, 3-pentyl, hexyl among others. In one embodiment, useful alkyl groups are selected from straight chain $C_{1-4}$ alkyl groups and branched chain $C_{3-4}$ alkyl groups. Typical $C_{1-4}$ alkyl groups include methyl, ethyl, propyl, isopropyl, butyl, sec-butyl, tert-butyl, iso-butyl.

Useful cycloalkyl groups are selected from saturated cyclic hydrocarbon groups containing one to three rings having from three to twelve carbon atoms (i.e., $C_3$-$C_{12}$ cycloalkyl) or the number of carbons designated. In one embodiment, the cycloalkyl has one or two rings. In another embodiment, the cycloalkyl is a $C_3$-$C_8$ cycloalkyl. Exemplary cycloalkyl groups include cyclopropyl, cyclobutyl, cyclopentyl, cyclohexyl, cycloheptyl, cyclooctyl, norbornyl, decalin, adamantyl and the like.

Useful cycloalkenyl groups are selected from partially unsaturated (containing one or two double bonds) cyclic hydrocarbon groups containing one to three rings having from four to twelve carbon atoms (i.e., $C_4$-$C_{12}$ cycloalkenyl) or the number of carbons designated. In one embodiment, the cycloalkenyl has one or two rings. In another embodiment, the cycloalkenyl is a $C_3$-$C_8$ cycloalkyl. In one embodiment, the cycloalkenyl group contains one double bond. Exemplary cycloalkenyl groups containing one double bond include cyclobutenyl, cyclopentenyl, cyclohexenyl, cycloheptenyl, cyclooctenyl, cyclononenyl, cyclodecenyl, among others. In another embodiment, the cycloalkenyl group contains two double bonds. Preferably, the cycloalkenyl groups containing two double bonds have from five to twelve carbon atoms (i.e., $C_5$-$C_{12}$ cycloalkadienyl). Exemplary cycloalkenyl groups having two double bonds include cyclopentadienyl, cyclohexadienyl, cycloheptadienyl, cyclooctadienyl, cyclononadienyl, cyclodecadienyl, among others.

Useful alkenyl groups are selected from straight-chain and branched-chain $C_{2-6}$ alkenyl groups, preferably $C_{2-4}$ alkenyl. Typical $C_{2-6}$ alkenyl groups include ethenyl, propenyl, isopropenyl, butenyl, sec-butenyl, pentenyl, and hexenyl. Typical $C_{2-4}$ alkenyl groups include ethenyl, propenyl, isopropenyl, butenyl, and sec-butenyl.

Useful alkynyl groups are selected from straight-chain and branched-chain $C_{2-6}$ alkynyl groups, preferably $C_{2-4}$ alkynyl. Typical $C_{2-6}$ alkynyl groups include ethynyl, propynyl, butynyl, 2-butynyl, pentynyl, and hexynyl groups. Typical $C_{2-4}$ alkynyl groups include ethynyl, propynyl, butynyl, and 2-butynyl groups.

Useful haloalkyl groups include any of the above-mentioned $C_{1-10}$ alkyl groups substituted by one or more fluorine, chlorine, bromine or iodine atoms (e.g., fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups).

Useful hydroxyalkyl groups include any of the above-mentioned $C_{1-10}$ alkyl groups substituted by one or more hydroxy groups, such as monohydroxyalkyl and dihydroxyalkyl groups (e.g., hydroxymethyl, hydroxyethyl, hydroxypropyl, hydroxybutyl and hydroxypentyl groups, and especially 2-hydroxy-3,3-dimethylbut-2-yl, 2-hydroxypent-2-yl, 2-hydroxyprop-2-yl, hydroxymethyl, 1-hydroxyethyl, 2-hydroxyethyl, 1,2-dihydroxyethyl, 2-hydroxypropyl, 3-hydroxypropyl, 2,3-dihydroxypropyl, 3-hydroxybutyl, 4-hydroxybutyl, 2-hydroxy-1-methylpropyl, and 1,3-dihydroxyprop-2-yl).

Useful alkoxy groups include oxygen substituted by one of the $C_{1-10}$ alkyl groups mentioned above (e.g., methoxy, ethoxy, propoxy, iso-propoxy, butoxy, tert-butoxy, iso-butoxy, sec-butoxy, pentyloxy, hexyloxy, heptyloxy, octyloxy, nonyloxy and decyloxy).

Useful alkoxyalkyl groups include any of the above-mentioned $C_{1-10}$ alkyl groups substituted with any of the above-mentioned alkoxy groups (e.g., methoxymethyl, methoxyethyl, methoxypropyl, methoxybutyl, ethoxymethyl, 2-ethoxyethyl, 3-ethoxypropyl, 4-ethoxybutyl, propoxymethyl, iso-propoxymethyl, 2-propoxyethyl, 3-propoxypropyl, butoxymethyl, tert-butoxymethyl, isobutoxymethyl, sec-butoxymethyl, and pentyloxymethyl).

Useful haloalkoxy groups include oxygen substituted by one of the $C_{1-10}$ haloalkyl groups mentioned above (e.g., fluoromethoxy, difluoromethoxy, trifluoromethoxy, and 2,2,2-trifluoroethoxy).

Useful (cycloalkyl)alkyl groups include any of the above-mentioned $C_{1-10}$ alkyl groups substituted with any of the above-mentioned cycloalkyl groups (e.g., (cyclopropyl)methyl, 2-(cyclopropyl)ethyl, (cyclopropyl)propyl, (cyclobutyl)methyl, (cyclopentyl)methyl, (cyclohexyl)methyl, and the like).

Useful (cycloalkyl)alkenyl groups include any of the above-mentioned $C_{2-6}$ alkenyl groups substituted with any of the above-mentioned cycloalkyl groups.

Useful (cycloalkenyl)alkyl groups include any of the above-mentioned $C_{1-10}$ alkyl groups substituted with any of the above-mentioned cycloalkenyl groups (e.g., (cyclobutenyl)methyl, 2-(cyclobutenyl)ethyl, (cyclobutenyl)propyl, (cyclopentenyl)methyl, (cyclohexenyl)methyl, (cyclopentadienyl)methyl, and the like).

Useful (cycloalkenyl)alkenyl groups include any of the above-mentioned $C_{2-6}$ alkenyl groups substituted with any of the above-mentioned cycloalkenyl groups.

Useful aryl groups are $C_{6-14}$ aryl, preferably $C_{6-12}$ aryl, and especially $C_{6-10}$ aryl. Typical $C_{6-14}$ aryl groups include phenyl, naphthyl, phenanthryl, anthracyl, indenyl, azulenyl, biphenyl, biphenylenyl, and fluorenyl groups, more preferably phenyl, naphthyl, and biphenyl groups.

Useful aryloxy groups include oxygen substituted by one of the aryl groups mentioned above (e.g., phenoxy).

Useful arylalkyl groups include any of the above-mentioned $C_{1-10}$ alkyl groups substituted by any of the above-mentioned aryl groups (e.g., benzyl, phenethyl, and the like).

Useful (arylalkyl)carbonyl groups include a carbonyl group substituted by any of the above-mentioned arylalkyl groups.

Useful aralkyloxy or arylalkoxy groups include oxygen substituted by one of the above-mentioned arylalkyl groups (e.g., benzyloxy).

Useful (arylalkoxy)carbonyl groups include a carbonyl group substituted by any of the above-mentioned arylalkoxy groups (e.g., (benzyloxy)carbonyl).

The term "heteroaryl" or "heteroaromatic" as employed herein refers to groups having 5 to 14 ring atoms, with 6, 10 or 14 π electrons shared in a cyclic array, and containing carbon atoms and 1, 2, or 3 oxygen, nitrogen or sulfur heteroatoms, or 4 nitrogen atoms. Examples of heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. Typical heteroaryl groups include thienyl (e.g., thien-2-yl and thien-3-yl), furyl (e.g., 2-furyl and 3-furyl), pyrrolyl (e.g., pyrrol-1-yl, 1H-pyrrol-2-yl and 1H-pyrrol-3-yl), imidazolyl (e.g., imidazol-1-yl, 1H-imidazol-2-yl and 1H-imidazol-4-yl), tetrazolyl (e.g., tetrazol-1-yl and tetrazol-5-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl).

Useful heteroarylalkyl groups include any of the above-mentioned $C_{1-10}$ alkyl groups substituted by any of the above-mentioned heteroaryl groups (e.g., (thien-2-yl)methyl, 2-furylmethyl, (pyrrol-1-yl)methyl, 2-(1H-pyrrol-2-yl)ethyl and the like).

Useful heteroarylalkenyl groups include any of the above-mentioned $C_{2-6}$ alkenyl groups substituted by any of the above-mentioned heteroaryl groups.

Useful heteroarylalkoxy groups include oxygen substituted by one of the above-mentioned heteroaryl groups.

Useful (heteroarylalkoxy)carbonyl groups include a carbonyl group substituted by any of the above-mentioned heteroarylalkoxy groups.

The terms "heterocyclic" and "heterocyclo" are used herein to mean saturated or partially unsaturated 3-7 membered monocyclic, or 7-10 membered bicyclic ring system, which consist of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on a carbon atom or on a nitrogen atom if the resulting compound is stable. In one embodiment, the 3- to 7-membered monocyclic heterocyclic ring is either a saturated, or unsaturated non-aromatic ring. A 3-membered heterocyclo can contain up to 1 heteroatom, a 4-membered heterocyclo can contain up to 2 heteroatoms, a 5-membered heterocyclo can contain up to 4 heteroatoms, a 6-membered heterocyclo can contain up to 4 heteroatoms, and a 7-membered heterocyclo can contain up to 5 heteroatoms. Each heteroatom is independently selected from nitrogen, which can be quaternized; oxygen; and sulfur, including sulfoxide and sulfone. The 3- to 7-membered heterocyclo can be attached via a nitrogen or carbon atom. A 7- to 10-membered bicyclic heterocyclo contains from 1 to 4 heteroatoms independently selected from nitrogen, which can be quaternized; oxygen; and sulfur, including sulfoxide and sulfone. The 7- to 10-membered bicyclic heterocyclo can be attached via a nitrogen or carbon atom. Examples of the heterocyclic rings include, but are not limited to, pyrrolidinyl, piperidinyl, piperazinyl, morpholinyl, imidazolinyl, pyrazolidinyl, tetrahydrofuranyl, oxazolidinyl, 2-oxooxazolidinyl, tetrahydrothienyl, imidazolidinyl, hexahydropyrimidinyl, benzodiazepines, and the like.

Useful (heterocyclo)alkyl groups include any of the above-mentioned $C_{1-10}$ alkyl groups substituted by any of the above-mentioned heterocyclic groups (e.g., (pyrrolidin-2-yl)methyl, (pyrrolidin-1-yl)methyl, (piperidin-1-yl)methyl, (morpholin-1-yl)methyl, (2-oxooxazolidin-4-yl)methyl, 2-(2-oxooxazolidin-4-yl)ethyl, (2-oxoimidazolidin-1-yl)methyl, (2-oxo-imidazolidin-1-yl)ethyl, (2-oxo-imidazolidin-1-yl)propyl, and the like).

Useful (heterocyclo)alkenyl groups include any of the above-mentioned $C_{2-6}$ alkenyl groups substituted by any of the above-mentioned heterocyclic groups.

As used herein, the term "aminocarbonyl" refers to —C(=O)NH$_2$.

Useful alkylcarbonyl groups include a carbonyl group, i.e., —C(=O)—, substituted by any of the above-mentioned $C_{1-10}$ alkyl groups.

Useful alkoxycarbonyl groups include a carbonyl group substituted by any of the above-mentioned alkoxy groups (i.e., —C(=O)O-alkyl) (e.g., methoxycarbonyl, ethoxycarbonyl, propoxycarbonyl, iso-propoxycarbonyl, butoxycarbonyl, tert-butoxycarbonyl, iso-butoxycarbonyl, sec-butoxycarbonyl, and pentyloxycarbonyl).

Useful arylcarbonyl groups include a carbonyl group substituted by any of the above-mentioned aryl groups (e.g., benzoyl).

Useful alkylcarbonyloxy or acyloxy groups include oxygen substituted by one of the above-mentioned alkylcarbonyl groups.

Useful alkylcarbonylamino or acylamino groups include any of the above-mentioned alkylcarbonyl groups attached to an amino nitrogen, such as methylcarbonylamino.

As used herein, the term "carboxamido" refers to a radical of formula —C(=O)NR$^{11}$R$^{12}$, wherein R$^{11}$ and R$^{12}$ are each independently hydrogen, optionally substituted $C_{1-10}$ alkyl, or optionally substituted aryl. Exemplary carboxamido groups include —CONH$_2$, —CON(H)CH$_3$, —CON(CH$_3$)$_2$, and —CON(H)Ph and the like Useful alkylaminocarbonyl and dialkylaminocarbonyl groups are any of the above-mentioned carboxamido groups, where R$^{11}$ is H and R$^{12}$ is $C_{1-10}$ alkyl or where R$^{13}$ and R$^{14}$ are each independently selected from a $C_{1-10}$ alkyl group, respectively.

As used herein, the term "sulfonamido" refers to a radical of formula —SO$_2$NR$^{11}$R$^{12}$, wherein R$^{11}$ and R$^{12}$ are each independently hydrogen, optionally substituted $C_{1-10}$ alkyl, or optionally substituted aryl. Exemplary sulfonamido groups include —SO$_2$NH$_2$, —SO$_2$N(H)CH$_3$, —SO$_2$N(H)Ph and the like.

Useful mercaptoalkyl groups include any of the above-mentioned $C_{1-10}$ alkyl groups substituted by a —SH group.

As used herein, the term "carboxy" refers to —COOH.

Useful carboxyalkyl groups include any of the above-mentioned $C_{1-10}$ alkyl groups substituted by —COOH.

As used herein, the terms "hydroxyl" or "hydroxy" refer to —OH.

As used herein, the term "cyano" refers to —CN.

As used herein, the term "formyl" refers to —C(=O)H.

As used herein, the term "ureido" refers to —NH—C(=O)—NH$_2$.

As used herein, the term "azido" refers to —N$_3$.

The term "mother liquor" as used herein means the part of a solution that is left over after crystallization.

The term "ambient temperature" as used herein means the temperature of the surroundings. The ambient temperature indoors is the same as room temperature, which is from about 20° C. to about 25° C.

The term "about," as used herein in connection with a measured quantity, refers to the normal variations in that measured quantity, as expected by the skilled artisan making the measurement and exercising a level of care commensurate with the objective of measurement and the precision of the measuring equipment.

As used herein, the term "optionally substituted" refers to a group that may be unsubstituted or substituted.

Optional substituents on optionally substituted groups, when not otherwise indicated, include one or more groups, typically 1, 2, or 3 groups, independently selected from the group consisting of halo, halo($C_{1-6}$)alkyl, aryl, heterocycle, cycloalkyl, $C_{1-6}$ alkyl, $C_{2-6}$ alkenyl, $C_{2-6}$ alkynyl, aryl($C_{1-6}$)alkyl, aryl($C_{2-6}$)alkenyl, aryl($C_{2-6}$)alkynyl, cycloalkyl($C_{1-6}$)alkyl, heterocyclo($C_{1-6}$)alkyl, hydroxy($C_{1-6}$)alkyl, carboxy($C_{1-6}$)alkyl, alkoxy($C_{1-6}$)alkyl, nitro, ureido, cyano, alkylcarbonylamino, hydroxy, thiol, alkylcarbonyloxy, aryloxy, ar($C_{1-6}$)alkyloxy, carboxamido, sulfonamido, azido, $C_{1-6}$ alkoxy, halo($C_{1-6}$)alkoxy, carboxy, aminocarbonyl, (=O), and mercapto($C_{1-6}$)alkyl groups mentioned above. Preferred optional substituents include halo, halo($C_{1-6}$)alkyl, hydroxy($C_{1-6}$)alkyl, hydroxy, nitro, $C_{1-6}$ alkyl, $C_{1-6}$ alkoxy, and halo($C_{1-6}$)alkoxy.

Some of the compounds disclosed herein may contain one or more asymmetric centers and may thus give rise to enantiomers, diastereomers, and other stereoisomeric forms, such as epimers. The present invention is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "under conditions conducive to precipitation" refers to conditions which are suitable to induce or facilitate precipitation of the desired compound.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "chiral" refers to a carbon atom to which four different groups are attached.

The term "chiral" in the context of the present invention also refers to a compound of group, exhibiting a "chiral center", such as a chiral acid. Exemplary chiral acids are lactic acid, tartric acid, and the like.

The term "achiral" in the context of the present invention refers to a compound of group, wherein no "chiral center" is present. An example for achiral compounds are achiral acids, such as acetic acid, trifluoroacetic acid, tribromoacetic acid, trichloroacetic acid, fumaric acid, maleic acid, and the like.

The term "epimer" refers to diastereomers that have opposite configuration at only one of two or more tetrahedral sterogenic centres present in the respective molecular entities.

The term "stereogenic center" is an atom, bearing groups such that an interchanging of any two groups leads to a stereoisomer.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

Open terms such as "include," "including," "contain," "containing" and the like mean "comprising."

Synthesis of Compounds

Compounds of Formula I can be prepared as shown in the schemes below. The synthesis of the compounds usually starts with a Diels-Alder reaction of thebaine or oripavine with dienophile, for example, a vinyl ketone under formation of the 7α/7β-epimer mixture A-2 (7α-epimer A$^a$-2 and 7β-epimer A$^b$-2) (Scheme 2).

Scheme 2
Synthesis of 7α/7β-epimer mixture of compounds of Formula I

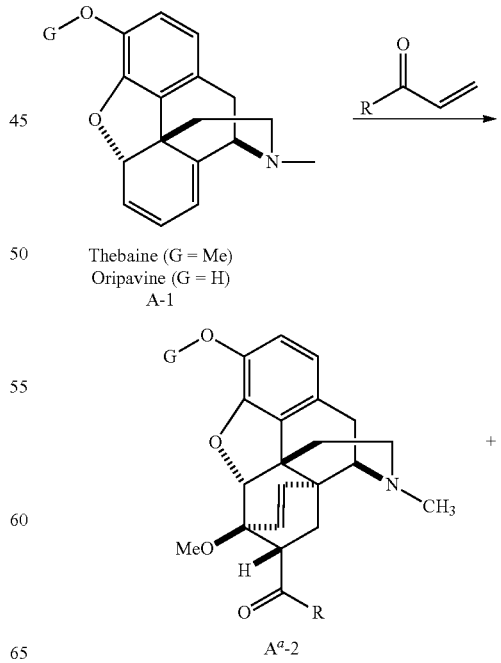

Thebaine (G = Me)
Oripavine (G = H)
A-1

A$^a$-2

-continued

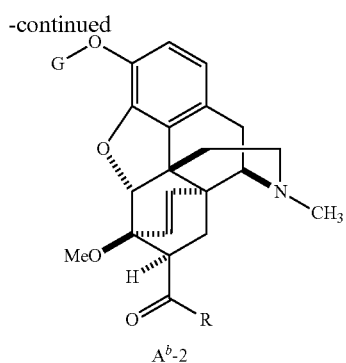

$A^b$-2

In Scheme 2, G is $R^1$ or a hydroxyl protecting group as defined above for Formula I and R is alkyl, optionally substituted with 1, 2, or 3, substituents each independently selected from the group consisting of hydroxy, hydroxyalkyl, halo, haloalkyl, alkoxy, alkylcarbonyl, and alkoxycarbonyl, respectively, or a functional group that can be converted to these groups.

The 7α/7β-epimer mixture of compounds of Formula I, i.e., the mixture of epimers $A^a$-2 and $A^b$-2, can be synthesized by methods described in the art, for example, in Marton J., et al., *Synthetic Communications* 25(6):829-848 (1995) and Bentley, K. W., *Journal of American Chemical Society* 89(13):3267-3273 (1967). Usually, the alpha (a) epimer $A^a$-2 is formed as the major component. The 7α/7β-epimer mixture of the ketone A-2 can then be converted further through a series of transformations, which may include hydrogenation, N- and/or O-demethylation, Grignard or lithium alkyl addition as shown in Scheme 3 below as described, for example, in Bentley, K. W., et al., *Journal of American Chemical Society* 89(13):3273-3280 (1967); Bentley, K. W., and Hardy, D. G., *Journal of American Chemical Society* 89(13):3281-3292 (1967); Marton, J., et al., *Monatshefte für Chemie* 125:1229-1239 (1994).

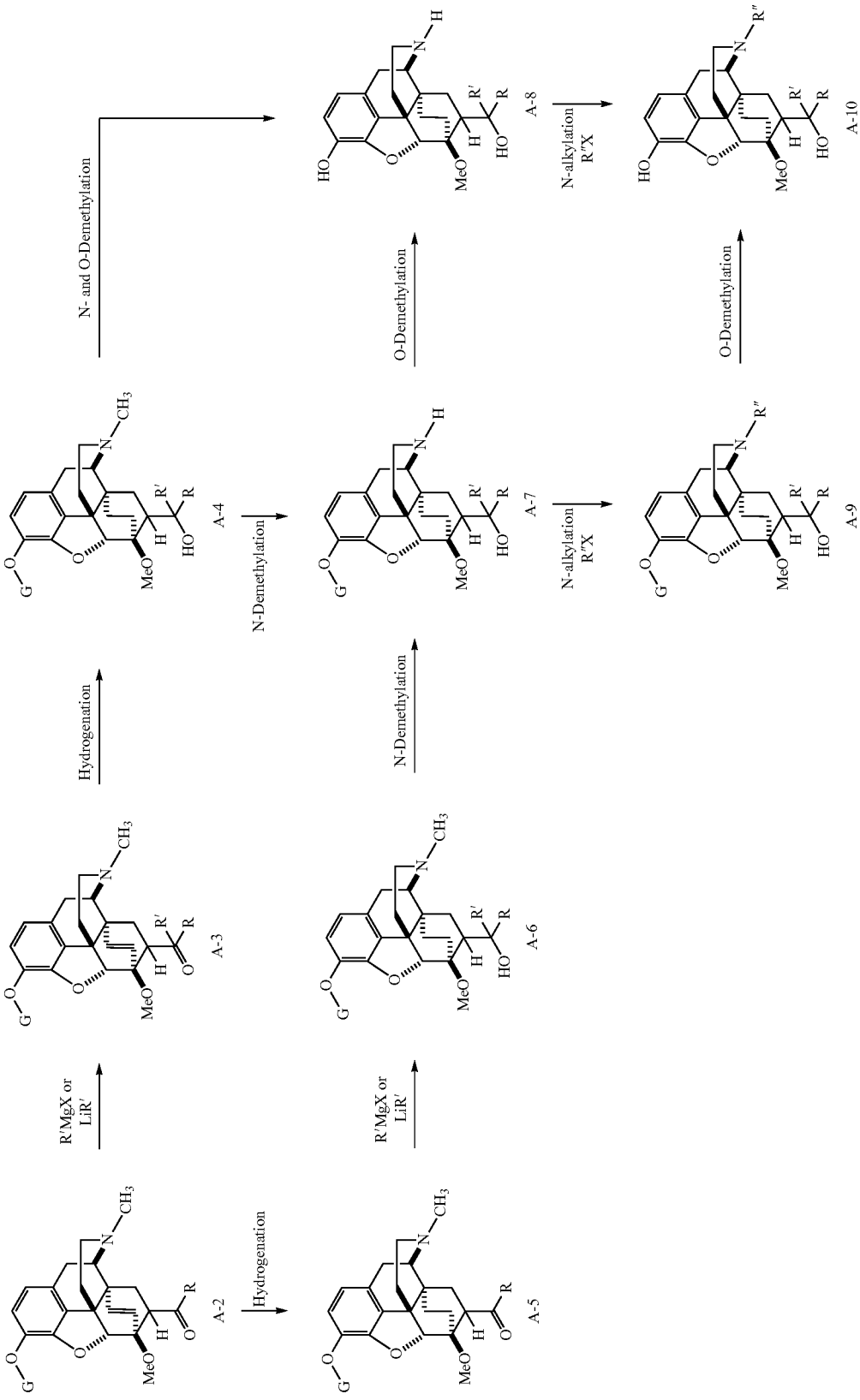

In Scheme 3, G is $R^1$ or a hydroxyl protecting group PG as defined above for Formula I, R and R' are each independently alkyl, optionally substituted with 1, 2, or 3, substituents each independently selected from the group consisting of hydroxy, halo, haloalkyl, alkoxy, alkylcarbonyl, and alkoxycarbonyl, respectively, or are functional groups that can be converted to these groups. R" is as defined above for $R^2$ or a group that can be converted to $R^2$. X is halogen or tosylate.

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

The following HPLC methods 1 and 2 were used:
HPLC Method 1
Column: Phenomenex Synergy Polar-RP, 50×3.0 mm, 2.5
Detection: UV 240 nm
Injection Volume: 2.0 µL
Flow Rate: 0.8 mL/min
Column Temperature: Ambient
Run Time: 15 min
Mobile Phase A: 0.025% TFA in water
Mobile Phase B: 0.025% TFA in acetonitrile
Gradient Profile:

|   | Time  | Flow | % A | % B |
|---|-------|------|-----|-----|
| 1 | 0.00  | 0.8  | 90  | 10  |
| 2 | 5.00  | 0.8  | 89  | 11  |
| 3 | 12.00 | 0.8  | 45  | 55  |
| 4 | 12.01 | 0.8  | 90  | 10  |
| 5 | 15.00 | 0.8  | 90  | 10  |

HPLC Method 2
Column: Phenomenex Synergy Polar-RP, 50×3.0 mm, 2.5 µm
Detection: UV 240 nm
Injection Volume: 5.0 µL
Flow Rate: 1.5 mL/min
Column Temperature: Ambient
Run Time: 25 min
Mobile Phase A: 0.025% TFA in water
Mobile Phase B: 0.025% TFA in acetonitrile
Gradient Profile:

|   | Time | Flow | % A  | % B  | % C | % D | Curve |
|---|------|------|------|------|-----|-----|-------|
| 1 | 0.00 | 1.50 | 95.0 | 5.0  | 0.0 | 0.0 | 6     |
| 2 | 20   | 1.50 | 35.0 | 65.0 | 0.0 | 0.0 | 6     |
| 3 | 21   | 1.50 | 95.0 | 5.0  | 0.0 | 0.0 | 6     |
| 4 | 25   | 1.50 | 95.0 | 5.0  | 0.0 | 0.0 | 6     |

Example 1

Separation of a mixture containing 1-[(5α,7α)-4,5-epoxy-3-hydroxy-6-methoxy-17-methyl-6,14-ethenomorphinan-7-yl]ethanone (1) and 1-[(5α,7β)-4,5-epoxy-3-hydroxy-6-methoxy-17-methyl-6,14-ethenomorphinan-7-yl]ethanone (2)

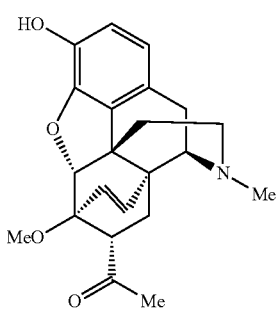

1

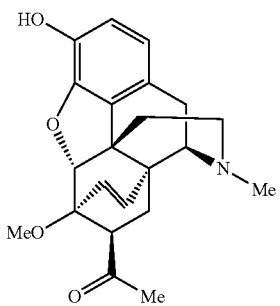

2

General Procedure:

Compounds 1 and 2 were mixed in the corresponding solvent in a 1:1 ratio and 0.6 or 1.2 equivalents (based on total 6α,14α-ethenomorphinan content) of the corresponding acid was added. In case of a precipitation, the precipitate was isolated and analyzed by HPLC analysis (HPLC method 1). From the HPLC analysis of the precipitate and the mother liquor, the amount of compound 1 and compound 2 in each fraction was calculated and the recovery of compound 2 in the isolated precipitate was determined.

To a vial was added compound 1 (0.1 g), compound 2 (0.1 g), and solvent (6 mL). The mixture was heated at 60° C. until most or all solid dissolved. To the vial was added 1.1 or 0.6 equivalents (based on the total amine content) of the acid. The mixture was allowed to cool to ambient temperature and was stirred overnight. The precipitated product was filtered, and both the solid as well as the mother liquor were analyzed by HPLC, and the yield and recovery were calculated. Tables 1 and 2 show the results of the tested solvent and acid combinations in the presence of 0.6 eq. acid and 1.1 eq. acid, respectively.

TABLE 1

Purity and recovery of isolated salts of compound 2 with 0.6 eq. acid

| | | Precipitate | | | | Mother liquor | |
| --- | --- | --- | --- | --- | --- | --- | --- |
| Solvent | Acid | Ratio[1] α:β (%) | Yield[2] (mg) | Recovery[2] (%) | Purify (%) | Ratio[1] α:β (%) | Yield[2] (mg) |
| 1 MeOH | AcOH | 1.7:98.3 | 57 | 56.3 | 98.3 | 69.2:30.6 | 143 |
| 2 EtOH | TFA | 24.4:75.6 | 118 | 89.2 | 75.6 | 86.5:13.2 | 82 |
| 3 n-PrOH | TFA | 29.8:70.2 | 135 | 95.2 | 70.2 | 92.0:7.4 | 65 |
| 4 IPA | TFA | 34.1:65.8 | 147 | 97.3 | 65.8 | 94.3:5.1 | 53 |
| 5 EtOH | Maleic | 25.6:74.4 | 118 | 87.6 | 74.4 | 85.0:15.0 | 82 |
| 6 n-PrOH | Maleic | 33.0:67.0 | 142 | 95.2 | 67.0 | 90.7:8.2 | 58 |
| 7 toluene | Maleic | 35.2:64.8 | 148 | 95.7 | 64.8 | 91.2:8.2 | 52 |
| 8 EtOH | Fumaric | No precip. | NA | NA | NA | 50:50 | NA |
| 9 n-PrOH | Fumaric | No precip. | NA | NA | NA | 50:50 | NA |
| 10 toluene | Fumaric | 8.0:92.0 | 35 | 32.4 | 91.9 | 57.9:41 | 165 |

[1]by HPLC analysis (HPLC method 1);
[2]based on free base; calculated from the epimer ratios in the precipitate and the mother liquor

TABLE 2

Purity and recovery of isolated salts of compound 2 with 1.1 eq. acid

| | | Precipitate | | | | Mother liquor | |
| --- | --- | --- | --- | --- | --- | --- | --- |
| Solvent | Acid | Ratio[1] α:β (%) | Yield[2] (mg) | Recovery[2] (%) | Purify (%) | Ratio[1] α:β (%) | Yield[2] (mg) |
| 1 MeOH | AcOH | 1.3:98.7 | 45 | 44.4 | 98.7 | 64.3:35.7 | 155 |
| 2 EtOH | TFA | 46.2:53.8 | 177 | 95.2 | 53.8 | 78.7:21.2 | 23 |
| 3 n-PrOH | TFA | 4.1:96.9 | 97 | 94.0 | 96.9 | 94.6:5.4 | 103 |
| 4 IPA | TFA | 4.8:95.2 | 100 | 95.2 | 95.2 | 96.0:4.0 | 100 |
| 5 EtOH | Maleic | 4.3:95.7 | 93 | 89.0 | 95.7 | 89.7:10.3 | 107 |
| 6 n-PrOH | Maleic | 8.7:91.3 | 100 | 91.3 | 91.3 | 91.3:8.7 | 100 |
| 7 toluene | Maleic | None | | NA | NA | | |
| 8 n-PrOH | Fumaric | 49.8:50.2 | 187 | 93.9 | 50.2 | 52.9:47.1 | 13 |
| 9 toluene | Fumaric | 49.5:50.5 | 186 | 93.9 | 50.5 | 55.3:43.3 | 14 |
| 10 CPME | Fumaric | 49.5:50.5 | 197 | 99.5 | 50.5 | 83.0:16.5 | 3 |

[1]by HPLC analysis (HPLC method 1);
[2]based on free base; calculated from epimer ratios in the precipitate and the mother liquor The results of Table 2 show that when 1.1 equivalents of acid (especially trifluoro acetic acid (TFA) or maleic acid) is used in n-propanol, isopropanol (IPA), or ethanol, high recovery and high purity of the 7β-epimer are achieved. A moderate recovery, but high purity, is achieved in the mixture of methanol and 1.1 equivalents of acetic acid.

The results of Table 1 show that 0.6 equivalents of TFA or maleic acid in alcohol provides similar recoveries than those in Table 2, but a somewhat lower purity of the 7β-epimer. Using 0.6 equivalents of acid, a moderate recovery, but high purity, was achieved in methanol and acetic acid as well as toluene and fumaric acid.

Example 2

Separation of a mixture containing 1-[(5α,7α)-3-benzyloxy-4,5-epoxy-6-methoxy-17-methyl-6,14-ethenomorphinan-7-yl]ethanone (3) and 1-[(5α,7β)-3-benzyloxy-4,5-epoxy-6-methoxy-17-methyl-6,14-ethenomorphinan-7-yl]ethanone (4)

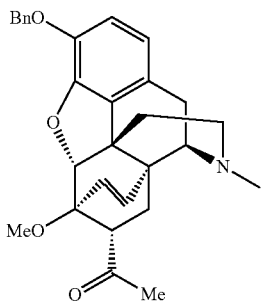

3

-continued

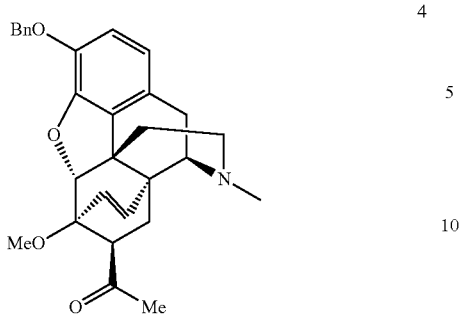

4

The separation of compounds 3 and 4 was conducted using the procedure as described in Example 1. The results are described in Table 3 (0.6 eq acid) and Table 4 (1.1 eq. acid).

TABLE 3

Purity and recovery of isolated salts of compound 4 with 0.6 eq. acid

| | | | Precipitate | | | Mother liquor | |
|---|---|---|---|---|---|---|---|
| | Solvent | Acid | Ratio[1] α:β (%) | Yield[2] (mg) | Recovery[2] (%) | Purify (%) | Ratio[1] α:β (%) | Yield[3] (mg) |
| 1 | MeOH | AcOH | 0.7:99.3 | 56 | 55.6 | 99.3 | 68.3:30.7 | 144 |
| 2 | EtOH | AcOH | 1.4:98.6 | 77 | 75.9 | 98.6 | 79.8:19.2 | 123 |
| 3 | n-PrOH | AcOH | 1.4:98.6 | 72 | 70.1 | 98.6 | 76.4:22.6 | 128 |
| 4 | IPA | AcOH | 3.4:96.6 | 87 | 84.4 | 96.6 | 85.5:14.5 | 113 |
| 5 | Toluene | Maleic | No precip. | NA | NA | NA | 50:50 | NA |
| 6 | CPME | Maleic | No precip. | NA | NA | NA | 50:50 | NA |
| 7 | EtOH | Fumaric | 1.6:98.4 | 36 | 35.4 | 98.4 | 59.9:39.1 | 164 |
| 8 | n-PrOH | Fumaric | 1.3:98.7 | 28 | 27.6 | 98.7 | 57.6:42.4 | 172 |
| 9 | IPA | Fumaric | 5.3:94.7 | 74 | 70.1 | 94.7 | 75.56:24.4 | 126 |

[1] by HPLC analysis (HPLC method 1);
[2] based on free base; calculated from epimer ratios in precipitate and mother liquor

TABLE 4

Purity and recovery of isolated salts of compound 4 with 1.1 eq. acid

| | | | Precipitate | | | Mother liquor | |
|---|---|---|---|---|---|---|---|
| | Solvent | Acid | Ratio[1] α:β (%) | Yield[2] (mg) | Recovery[2] (%) | Purify (%) | Ratio[1] α:β (%) | Yield[3] (mg) |
| 1 | MeOH | AcOH | 1.4:98.6 | 45 | 44.4 | 98.6 | 63.5:36.5 | 155 |
| 2 | EtOH | AcOH | 0.4:99.6 | 67 | 66.7 | 99.6 | 74.3:24.7 | 133 |
| 3 | n-PrOH | AcOH | 0.6:99.4 | 63 | 62.6 | 99.4 | 71.7:27.3 | 137 |
| 4 | IPA | AcOH | 1.7:98.3 | 83 | 81.4 | 98.1 | 83.5:15.5 | 117 |
| 5 | Toluene | Maleic | No precip. | NA | NA | NA | 50:50 | NA |
| 6 | CPME | Maleic | No precip. | NA | NA | NA | 50:50 | NA |
| 7 | EtOH | Fumaric | No precip. | NA | NA | NA | 50:50 | NA |
| 8 | n-PrOH | Fumaric | No precip. | NA | NA | NA | 50:50 | NA |
| 9 | IPA | Fumaric | 15.2:84.8 | 85 | 72.0 | 84.8 | 74.6:24.4 | 115 |

[1] by HPLC analysis (HPLC method 1);
[2] based on free base; calculated from epimer ratios in the precipitate and the mother liquor;

Tables 3 and 4 show that high recovery and high purity of the 7β-epimer was achieved with 0.6 and 1.1 equivalents of acetic acid in alcohols. Recovery seemed to increase with decreasing polarity. High purity and a somewhat lower recovery of the 7β-epimer was achieved with 0.6 equivalents of fumaric acid. Fumaric acid and IPA afforded a somewhat lower purity in 1.1 eq. of acid.

Example 3

Separation of a mixture containing (5α,7α)-4,5-epoxy-3-hydroxy-6-methoxy-17-methyl-6,14-ethenomorphinan-7-carbonitrile (5) and (5α,7β)-4,5-epoxy-3-hydroxy-6-methoxy-17-methyl-6,14-ethenomorphinan-7-carbonitrile (6)

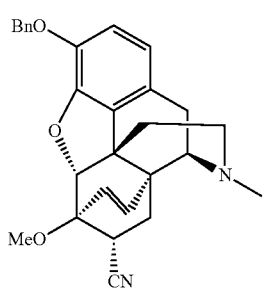

5

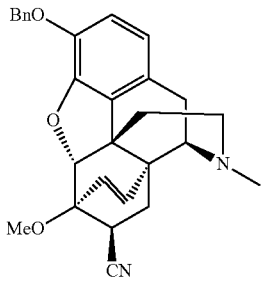

6

The separation of compounds 5 and 6 was conducted as described in Example 1 using HPLC method 2 instead of HPLC method 1. The results are described in Table 5 (0.6 eq acid) and Table 6 (1.1 eq. acid) below.

TABLE 5

Purity and recovery of isolated salts of compounds 5 and 6 with 0.6 eq. acid

| | | Precipitate | | | | Mother liquor | |
| --- | --- | --- | --- | --- | --- | --- | --- |
| Solvent | Acid | Ratio[1] α:β (%) | Yield[2] (mg) | Recovery[2] (%) | Purify (%) | Ratio[1] α:β (%) | Yield[3] (mg) |
| 1 EtOH | AcOH | No precip. | NA | 0 | NA | 50:50 | |
| 2 n-PrOH | AcOH | 3.9:96.1 | 59 | 56.7 | 96.1 | 69.2:30.8 | 141 |
| 3 IPA | AcOH | 4.9:95.1 | 61 | 58.0 | 95.1 | 69.3:30.4 | 139 |
| 4 EtOH | Maleic | 93.8:6.2[3] | 103 | 96.6 | 93.8 | 3.7:96.3 | 97 |
| 5 MeOH | Fumaric | 51.4:48.6 | 136 | 69.9 | 51.4 | 47.0:53.0 | 63 |
| 6 EtOH | Fumaric | 51.4:48.6 | 139 | 71.4 | 51.4 | 46.8:53.2 | 61 |
| 7 n-PrOH | Fumaric | 51.7:48.3 | 74 | 38.2 | 51.7 | 49.0:51.0 | 126 |

[1]by HPLC analysis (HPLC method 2);
[2]based on free base; calculated from epimer ratios in precipitate and mother liquor;
[3]7α-epimer is isolated

TABLE 6

Purity and recovery of isolated salts of compound 6 with 1.1 eq. acid

| | | Precipitate | | | | Mother liquor | |
| --- | --- | --- | --- | --- | --- | --- | --- |
| Solvent | Acid | Ratio[1] α:β (%) | Yield[2] (mg) | Recovery[2] (%) | Purify (%) | Ratio[1] α:β (%) | Yield[3] (mg) |
| 1 EtOH | AcOH | No precip. | 0 | 0 | NA | 50:50 | 200 |
| 2 n-PrOH | AcOH | 3.8:96.2[3] | 63 | 60 | 96.2 | 71.2:28.8 | 137 |
| 3 IPA | AcOH | 4.5:95.5[3] | 55 | 53 | 95.5 | 67.4:32.6 | 145 |
| 4 EtOH | Maleic | 54.4:45.6 | 170 | 92 | 54.4 | 24.8:75.2 | 30 |
| 5 MeOH | Fumaric | 52.5:47.5 | 91 | 48 | 52.5 | 47.9:52.1 | 109 |
| 6 EtOH | Fumaric | 52.3:47.7 | 179 | 93 | 52.3 | 50.3:49.7 | 21 |
| 7 n-PrOH | Fumaric | 53.1:46.9 | 29 | 15 | 53.1 | 46.7:53.3 | 171 |

[1]by HPLC analysis (HPLC method 2);
[2]based on free base; calculated from epimer ratios in precipitate and mother liquor;
[3]7β-epimer is isolated High recovery and high purity of the 7α-epimer was achieved with 0.6 eq. of maleic acid in ethanol, and the proportion of the 7β-increased in the mother liquor. n-PrOH and IPA with acetic acid gave high purity and moderate recovery of the 7β-epimer. No significant difference between 0.6 and 1.1 eq of acid was detected.

Example 4

Isolation of Compound 2 from a Mixture of Compound 2/Compound 1 in a 26:74 Ratio 21 g of a mixture containing compound 2 and compound 1 in a 26:74 ratio was suspended in IPA (350 mL) and heated to 70° C. After all solids were dissolved, the mixture was cooled to room temperature and trifluoroacetic acid (TFA) (1.7 g, 1.0 eq based on compound 2) was added dropwise. The mixture was stirred at ambient temperature overnight. The precipitate was filtered, washed with IPA (3×10 mL) and dried to give an off-white solid containing compound 2 and compound 1 in a 96.3:3.7 ratio. The crude product was suspended in IPA (10 mL) and heated at 80° C. and stirred for 1 h. After cooling to room temperature, the product was filtered and dried to give 3.5 g (49% recovery, 97.6% purity) of compound 7:

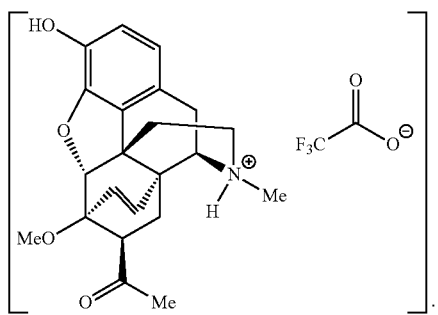

Compound 7 can be converted to its free base, compound 2, following the procedure described in Example 8 below.

Example 5

Isolation of Compound 2 from a Mixture of Compound 2/Compound 1 in a 45:55 Ratio 70 g of a mixture containing compound 2 and compound 1 in a 45:55 ratio was dissolved in hot IPA (1.2 L). After the solution was cooled to room temperature, TFA (6.4 mL, 1.0 eq. based on compound 2) was added dropwise. The mixture was kept at room temperature overnight and the precipitate was filtered and dried to afford 38.0 g of compound 2 TFA-salt with 88% purity. The crude product was then suspended in IPA (300 mL) and heated to reflux and stirred for 1 h. After cooling to room temperature, the product was filtered and dried to give 32.0 g (77% recovery, 97.8% purity) of compound 7.

Example 6

Isolation of Compound 2 from a Mixture of Compound 2/Compound 1 in a 46:54 Ratio 14.2 g of a mixture containing compound 2 and compound 1 in a 46:54 ratio was dissolved in hot IPA (140 mL). To the hot solution, TFA (1.3 mL, 1.0 eq. based on compound 2) was added dropwise. The mixture was cooled to room temperature and stirred overnight. The precipitate was filtered. The filter cake was washed with cold IPA (2×10 mL) and the product was dried to afford 8.0 g (93% recovery, 93.6% purity) of compound 7, which can be converted to compound 2 as described in Example 8.

Example 7

Isolation of Compound 2 from a Mixture of Compound 2/Compound 1 in a 60:40 Ratio 95 g of a mother liquor obtained after Diels-Alder reaction of oripavine and methyl vinyl ketone (MVK), containing in a 92% purity a mixture of compound 2 and compound 1 in a 60:40 ratio, was heated under reflux in IPA (500 mL). The mixture was cooled to ambient temperature and allowed to stir overnight. After filtering off an additional 6 g of compound 1, TFA (9.9 mL, 0.9 eq. based on compound 2) was added dropwise. The mixture was kept at room temperature overnight and the precipitate was filtered off. The crude product was then suspended in IPA (800 mL) and heated to 75° C. and stirred for 2 h. After cooling to room temperature, the product was filtered and dried to give 52.0 g (77% recovery, 97.3% purity) of compound 7, which can be converted to compound 2 as described in Example 8.

Example 8

Conversion of Compound 7 (TFA-Salt of Compound 2) to Compound 2

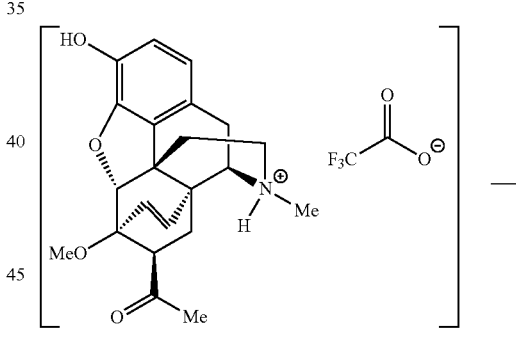

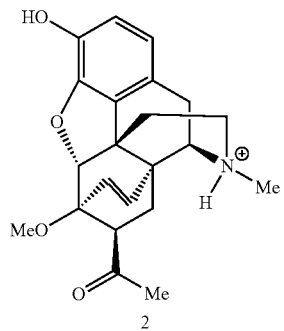

Method A:

To a mixture of 52 g of compound 7, in ethyl acetate (1000 mL) and water (300 mL) was added 28% NH₄OH and the pH of the mixture was adjusted to pH 9. The layers were separated and the aqueous layer was extracted with ethyl acetate (100 mL). The combined organic layers were washed with brine, dried over Na₂SO₄, and filtered. The filtrate was concentrated to dryness. The crude product was triturated in methanol (MeOH) (400 mL) and stirred for 30 minutes under reflux. After cooling to ambient temperature, the product was filtered off and dried to afford 38.6 g (97% recovery, 100% purity) of compound 2:

¹H NMR δ (400 MHz, CDCl₃): 6.59 (d, J=8 Hz, 1H), 6.47 (d, J=8.4 Hz, 1H), 6.02 (dd, J=8.8 Hz, 1.2 Hz, 1H), 4.88 (d, J=10 Hz, 1H), 5.02 (d, J=1.6 Hz, 1H), 3.59 (s, 3H), 3.22 (d, J=18 Hz, 1H), 3.16 (d, J=6.4 Hz, 1H), 3.02 (dd, J=11.2 Hz, 4.8 Hz, 1H), 2.88 (dd, J=12.8 Hz, 4.4 Hz, 1H), 2.76 (dt, J=12.8 Hz, 5.6 Hz, 1H), 2.55 (dd, J=11.6 Hz, 5.2 Hz, 1H), 2.44-2.38 (m, 2H), 2.36 (s, 3H), 2.30 (s, 3H), 1.66-1.61 (m, 1H), 1.42 (dd, J=12.8 Hz, 11.2 Hz, 1H). LC/MS (ESI): m/z=368.1 [M+H]⁺ (Calc: 367.4).

Alternative Method B:

Compound 7 (17.0 g) was suspended in H₂O (350 mL) and the pH of the mixture was adjusted to 9 by dropwise addition of NH₄OH. The mixture was then stirred at room temperature for 1 h. The solids were filtered off and the filter cake was washed with H₂O (2×100 mL) and then dried to afford 12.5 g (96.3%) of compound 2 was obtained as an off-white solid.

Example 9

Isolation of Compound 2 from a Mixture of Compound 2/Compound 1 in a 68:32 Ratio and Salt Breaking 119 g of a mother liquor obtained after Diels-Alder reaction of oripavine and MVK, containing in a 97% purity a mixture of compound 2 and compound 1 in a 68:32 ratio, was heated under reflux in IPA (600 mL). Once a solution was formed, TFA (15.5 g, 1.0 eq. based on compound 2) was added dropwise. The mixture was cooled to room temperature and compound 7 was filtered off. The crude compound 7 (103 g) was added to a mixture of EtOAc (1.5 L) and water (400 mL). Ammonium hydroxide was added (~15 mL) and the pH was adjusted tp pH 9. The layers were separated and the aqueous layer was extracted with ethyl acetate (200 mL). The combined organic layers were washed with brine, dried over Na₂SO₄, and filtered. The crude product was triturated in MeOH (400 mL) and stirred for 30 minutes under reflux. After cooling to ambient temperature, the product was filtered off and dried to afford 44.6 g (60% recovery, 99% purity) of compound 2 as an off-white crystalline solid.

Example 10

Isolation of Compound 6 from a Mixture of Compound 5/Compound 6 in a 50:50 Ratio A mixture of compound 5 (5.0 g) and compound 6 (5.0 g) in IPA (300 mL) was heated to 60° C. After a clear solution was formed acetic acid (1.03 g, 0.6 equiv to total base) was added. The mixture was cooled to ambient temperature and stirred overnight. The product was filtered off and the cake was washed with IPA (50 mL). After drying, 1.8 g (88% recovery, 98.1% purity) of compound 6 (the 7β-epimer) acetate salt (compound 8) was obtained:

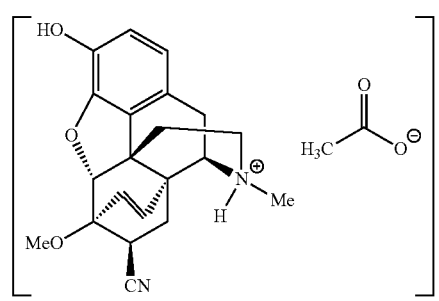

Example 11

Isolation of Compound 5 from a Mixture of Compound 5/Compound 6 in a 50:50 Ratio A mixture of compound 5 (5.0 g) and compound 6 (5.0 g) in ethanol (EtOH) (300 mL) was heated to 60° C. After a clear solution was formed maleic acid (1.99 g, 0.6 equiv to total base) was added. The mixture was cooled to 20° C. and stirred overnight. The product was filtered off and the cake was washed with ethanol (1000 mL). After drying, 5.9 g (31% recovery, 91.2% purity) of compound 5 (the 7α-epimer) maleate salt was obtained, while compound 6 maleate salt remained in the mother liquor (compound 9):

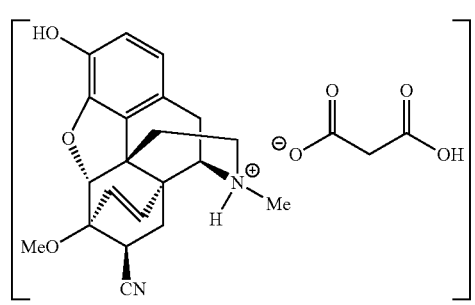

Example 12

Preparation of Compound 2

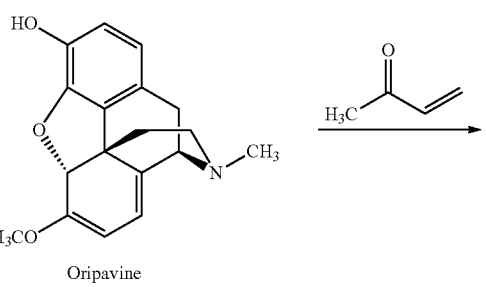

Oripavine

-continued

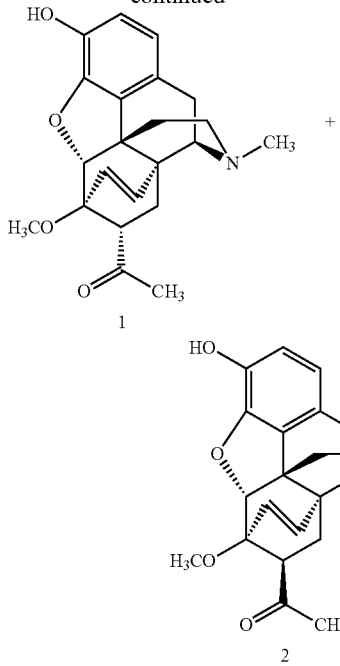

(a) A mixture of 1300 g of oripavine and methyl vinyl ketone (1.5 equiv) in isopropanol (3.25 L) was heated under reflux for 2 days. The mixture was cooled to 0° C. and then filtered. The filter cake was washed twice with iso-propanol (2×1 L) and then dried to afford 1444 g (89% yield, >99% purity) of compound 1:

$^1$H NMR δ (400 MHz, CDCl$_3$): 6.60 (d, J=8 Hz, 1H), 5.03 (d, J=7.6 Hz, 1H). 6.49 (dd, J=8.4 Hz, 1.2 Hz, 1H), 5.56 (d, J=9.2 Hz, 1H). 4.70 (bs, 1H), 4.59 (d, J=1.2 Hz, 1H), 3.57 (s, 3H), 3.22-3.19 (m, 2H), 2.96-2.90 (m, 2H), 2.53-2.50 (m, 1H), 2.44-2.37 (m, 2H), 2.36 (s, 3H), 2.13 (s, 3H), 2.01-1.95 (m, 1H), 1.87-1.83 (m, 1H), 1.38-1.32 (m, 1H).

LC/MS (ESI): m/z 368.1=[M+H]$^+$ (Calc: 367.4).

(b) The mother liquor from step (a), containing about 119.5 g of compound 1 and compound 2 in a 71:29 ratio was concentrated to about 3 L. The mixture was then heated to about 60° C. and TFA (1.1 equiv based on compound 2) was added. The mixture was seeded with compound 7 and cooled to 25° C. and stirred for 3 days. The mixture was filtered and the filter cake was washed with isopropanol (1 L) then dried to afford 28.8 g (64% yield) of compound 7, which can be converted to compound 2 as described in Example 8.

Example 13

Epimerization of Compound 1 with K$_2$CO$_3$

A mixture of compound 1 (32.5 g), K$_2$CO$_3$ (24.4, 2 equiv) in cyclopentyl methyl ether (CPME) (155 mL) and water (~3 mL) was heated to 75° C. for 48 h at which point HPLC analysis indicated 23% epimerization. The mixture was cooled to ambient temperature. Dichloromethane and water were added and the pH was adjusted to 7-8. The layers were separated and the organic layer was concentrated to dryness. The residue was triturated with ethyl acetate to afford 17.4 g of compound 1. The mother liquor, containing compounds 1 and 2 in a ratio of about 1:1, was concentrated to dryness. The residue was dissolved in IPA and treated with TFA as described in the examples above to afford 5.6 g (17.5%) of compound 2 after salt breaking.

Example 14

Synthesis of Compound 3

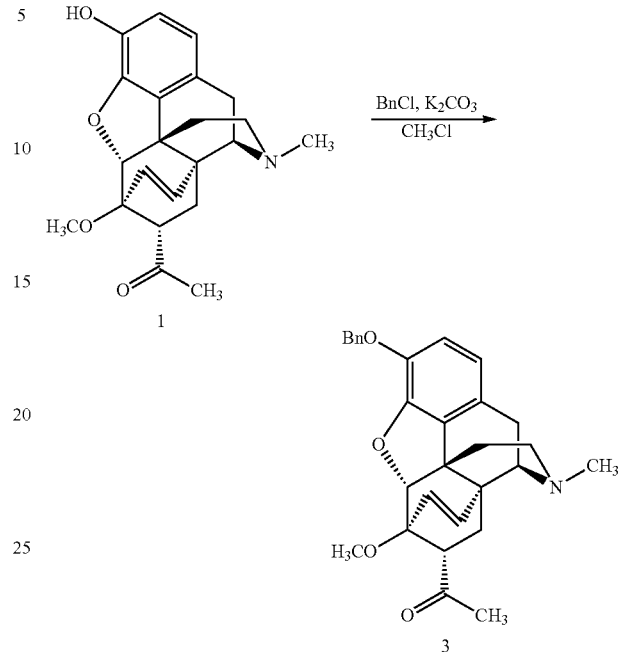

Compound 1 (15 g) was benzylated in chloroform with benzyl bromide (1.2 equiv) and potassium carbonate (1.2 eq). After heating the mixture under reflux for 6 hours, HPLC analysis indicated complete consumption of compound 1. The solids were filtered off and the filtrate was concentrated to afford a mixture of compound 2 and residual benzyl bromide. The residue was purified by column chromatography on silica eluting with dichloromethane to afford 20 g (100%) of compound 3 as a light yellow oil.

$^1$H NMR δ (300 MHz, CDCl$_3$): 7.41-7.26 (m, 5H), 6.65 (d, 1H), 6.48 (d, 1H), 5.90 (d, 1H), 5.57 (d, 1H), 5.16-5.06 (m, 2H), 4.57 (d, 1H), 3.60 (s, 3H), 3.22 (d, 1H), 3.18 (s, 1H), 2.95-2.86 (m, 2H), 2.57-2.47 (m, 1H), 2.44-2.35 (m, 5H), 2.14 (s, 3H), 2.02-1.92 (m, 1H), 1.86-1.78 (m, 1H), 1.41-1.33 (m, 1H).

LC/MS (ESI), m/z=458.3 [M+H]$^+$ (Calc: 457.6)

Example 15

Synthesis of Compound 4 after Epimerization of Compound 3

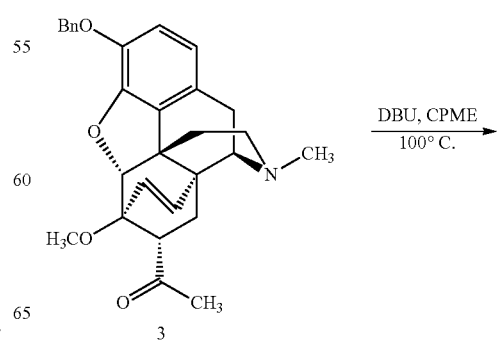

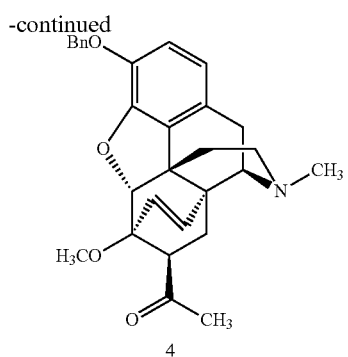

Compound 3 (20 g) was treated with 1.1 molar equivalents of DBU in cyclopentyl methyl ether (CPME) (200 mL) at 100° C. The progress of the reaction was monitored by HPLC. After about 3 days, conversion from compound 3 to compound 4 was about 22% based on HPLC. After work-up and column purification, 4.2 g of compound 4 (21% yield, 99.6A % pure) was isolated.

$^1$H NMR δ (300 MHz, CDCl$_3$): 7.41-7.26 (m, 5H), 6.64 (d, J=8.4 Hz, 1H), 6.45 (d, J=8.1 Hz, 1H), 6.03 (dd, J=9.3 Hz, 1.8 Hz, 1H), 5.47 (d, J=9.0 Hz, 1H), 5.17-5.06 (m, 2H), 5.00 (d, J=1.8 Hz, 1H), 3.61 (s, 3H), 3.21 (d, J=18.9 Hz, 1H), 3.15 (d, J=6.6 Hz, 1H), 2.99-2.79 (m, 3H), 2.62-2.52 (m, 1H), 2.42-2.33 (m, 5H), 2.30 (s, 3H), 1.66-1.61 (m, 1H), 1.40 (dd, J=12.2 Hz, 11.1 Hz, 1H).

LC/MS (ESI), m/z=458.4 [M+H]$^+$ (Calc: 457.6)

Example 16

Synthesis of Compound 4

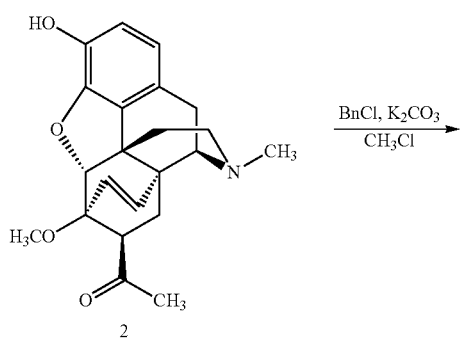

Compound 4 can also be synthesized analogous to the procedure described in Example 14 using compound 2 instead of Compound 1.

Example 17

Synthesis and Isolation of Compounds 5 and 6

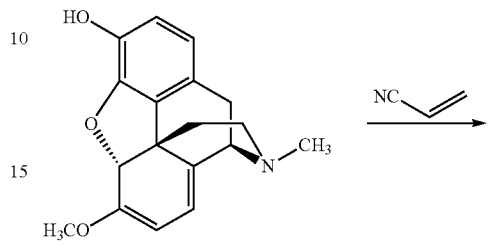

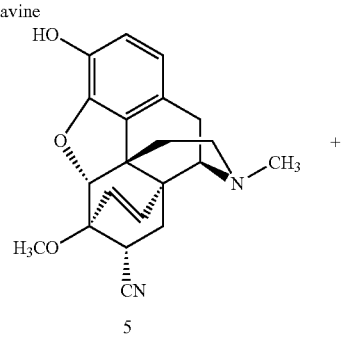

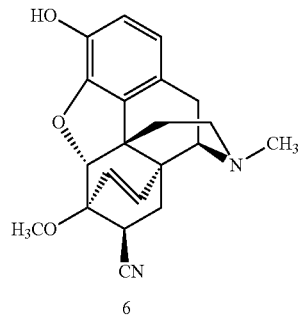

A mixture of oripavine (100 g) and acrylonitrile (1.1 equiv) in isopropanol (260 mL) was heated under in a 2-L pressure bottle at 100° C. overnight. The reaction mixture was allowed to cool to ambient temperature and sampled. HPLC analysis indicated consumption of oripavine and formation of two new products formed in about 1:1 ratio. The mixture was concentrated to dryness. The residue was redissolved in a minimal amount of dichloromethane (~400 mL) and purified by silica gel chromatography eluting with ethyl acetate/hexanes (1:1) to afford 16 g (14%) of compound 6 as the faster eluting epimer and 22 g (19%) of compound 5 as the slower eluting epimer. Both compounds were isolated as off-white solids. Compound 5 can also be crystallized from methanol, while compound 6 is more soluble in this solvent. Trituration of the crude ~1:1 mixture in methanol provided clean compound 6 after filtration. The mother liquor from the trituration contained compound 6 and compound 5 in about an 1:3 ratio Compound 6: $^1$H NMR δ (300 MHz, CDCl$_3$): 6.62 (d, J=8.1 Hz, 1H), 6.50 (d, J=8.1 Hz, 1H), 5.92 (dd, J=8.7 Hz, 1.8 Hz, 1H), 5.57 (d, J=9.6 Hz, 1H), 5.01 (d, J=1.2 Hz, 1H), 3.59 (s, 3H), 3.26-3.17 (m, 2H), 3.11 (dd, J=12.9 Hz, 3.3 Hz, 1H), 2.87 (dd, J=11.7 Hz, 3.6 Hz, 1H), 2.62-2.55 (m, 1H), 2.48-2.26 (s, 6H), 1.92-1.84 (m, 1H), 1.78-1.69 (m, 1H). LC/MS (ESI), m/z=351.0 [M+H]$^+$ (Calc: 350.4).

Compound 5: ¹H NMR δ (300 MHz, CDCl₃): 6.62 (d, J=8.1 Hz, 1H), 6.51 (d, J=8.4 Hz, 1H), 5.93 (dd, J=8.7 Hz, 1.8 Hz, 1H), 5.64 (d, J=9 Hz, 1H), 4.53 (d, J=1.8 Hz, 1H), 3.65 (s, 3H), 3.29-2.18 (m, 3H), 2.93-2.87 (m, 1H), 2.58-2.39 (m, 3H), 2.36 (s, 3H), 1.98-1.82 (m, 2H), 1.56 (dd, J=12.9 Hz, 5.4 Hz, 1H). LC/MS (ESI), m/z=351.0 [M+H]⁺ (Calc: 350.4).

Example 18

Synthesis and Isolation of Compound 10

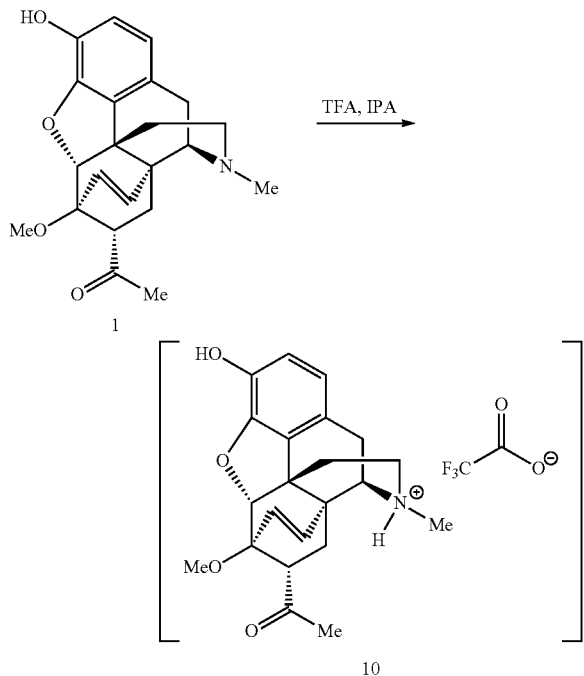

Compound 1 (20.9 g) was dissolved in IPA (350 mL) at 80° C. The solution was then cooled to 60° C. and TFA (5.2 mL, 1.2 eq.) was added dropwise. The mixture was cooled to ambient temperate and stirred overnight. The product was filtered off. The filter cake was washed with IPA (1×30 mL) and dried to afford 25.8 g of compound 10 (94.2%) as an off-white solid.

Example 19

Synthesis of Compound 7

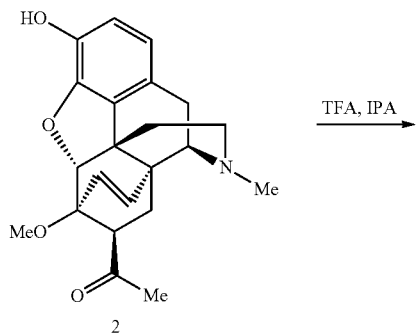

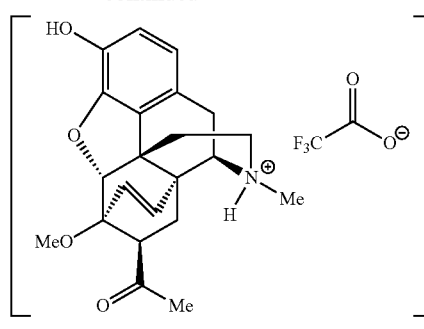

Compound 7 can be synthesized analogous to procedure described in Example 18 using compound 2 instead of compound 1.

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents, patent applications, and publications cited herein are fully incorporated by reference herein in their entirety.

What is claimed is:

1. A compound selected from the group consisting of

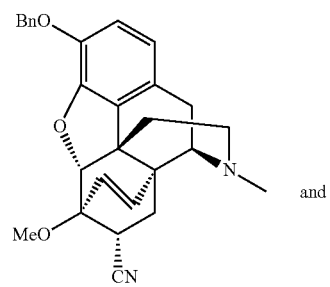 and

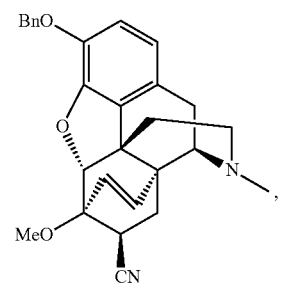

or a salt thereof.

2. A compound selected from the group consisting of
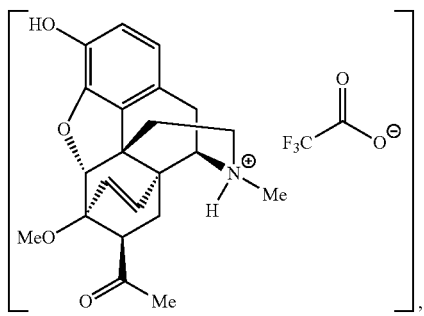
,
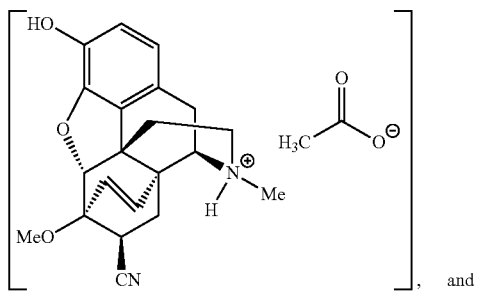
, and
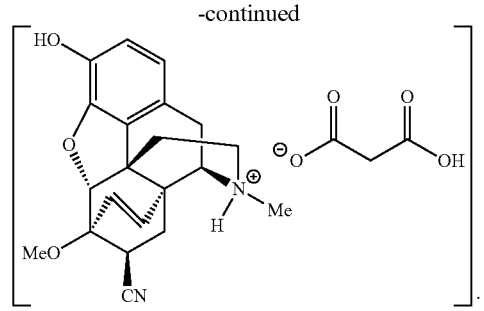
.
3. A compound, which is
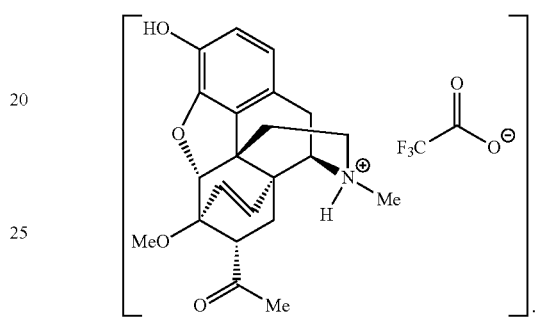
.
* * * * *